US011972561B2

(12) United States Patent
Athanasiou

(10) Patent No.: US 11,972,561 B2
(45) Date of Patent: Apr. 30, 2024

(54) AUTO-PULLBACK TRIGGERING METHOD FOR INTRACORONARY IMAGING APPARATUSES OR SYSTEMS USING BLOOD CLEARING

(71) Applicant: Canon U.S.A., Inc., Melville, NY (US)

(72) Inventor: Lampros Athanasiou, Medford, MA (US)

(73) Assignee: Canon U.S.A., Inc., Melville, NY (US)

( * ) Notice: Subject to any disclaimer, the term of this patent is extended or adjusted under 35 U.S.C. 154(b) by 517 days.

(21) Appl. No.: 17/343,502

(22) Filed: Jun. 9, 2021

(65) Prior Publication Data

US 2022/0044396 A1 Feb. 10, 2022

Related U.S. Application Data

(60) Provisional application No. 63/062,300, filed on Aug. 6, 2020.

(51) Int. Cl.
*G06T 7/00* (2017.01)
*G06T 5/70* (2024.01)
*G06T 7/136* (2017.01)

(52) U.S. Cl.
CPC ............ *G06T 7/0012* (2013.01); *G06T 5/70* (2024.01); *G06T 7/136* (2017.01);
(Continued)

(58) Field of Classification Search
CPC ............... A61B 5/0066; A61B 5/0084; G06T 2207/10068; G06T 2207/10101;
(Continued)

(56) References Cited

U.S. PATENT DOCUMENTS 6,292,681 B1 * 9/2001 Moore .................. A61B 8/12
600/463
6,763,261 B2 7/2004 Casscells, III et al.
(Continued)

FOREIGN PATENT DOCUMENTS

JP 2010/158343 A 7/2010
JP 2014526283 A 10/2014
(Continued)

OTHER PUBLICATIONS

Lida P. Hariri,"An automatic image processing algorithm for initiating and terminating intracoronary OFDI pullback," Aug. 10, 2010,Sep. 1, 2010 / vol. 1, No. 2 / Biomedical Optics Express 566, pp. 1-7.*
(Continued)

*Primary Examiner* — Omar S Ismail
(74) *Attorney, Agent, or Firm* — Canon U.S.A., Inc. I.P. Division

(57) ABSTRACT

One or more devices, systems, methods, and storage mediums for optical imaging medical devices, such as, but not limited to, Optical Coherence Tomography (OCT), single mode OCT, and/or multi-modal OCT apparatuses and systems, and methods and storage mediums for use with same, for triggering auto-pullback, including for devices or systems using blood clearing, are provided herein. Examples of applications include imaging, evaluating and diagnosing biological objects, such as, but not limited to, for Gastrointestinal, cardio and/or ophthalmic applications, and being obtained via one or more optical instruments, such as, but not limited to, optical probes, catheters, capsules and needles (e.g., a biopsy needle). Techniques provided herein also improve processing and imaging efficiency while achieving images that are more precise.

19 Claims, 23 Drawing Sheets

(52) U.S. Cl.
CPC ............... *G06T 2207/10101* (2013.01); *G06T 2207/20028* (2013.01); *G06T 2207/30021* (2013.01); *G06T 2207/30101* (2013.01)

(58) Field of Classification Search
CPC . G06T 2207/20028; G06T 2207/30021; G06T 2207/30101; G06T 2207/30168; G06T 2207/30242; G06T 5/70; G06T 7/0012; G06T 7/11; G06T 7/136; G06T 7/174
See application file for complete search history.

(56) References Cited

U.S. PATENT DOCUMENTS

| | | | |
|---|---|---|---|
| 7,366,376 B2 | 4/2008 | Shishkov et al. | |
| 7,382,464 B2 | 6/2008 | Everett et al. | |
| 7,447,408 B2 | 11/2008 | Bouma et al. | |
| 7,843,572 B2 | 11/2010 | Tearney et al. | |
| 7,872,759 B2 | 1/2011 | Tearney et al. | |
| 7,889,348 B2 | 2/2011 | Tearney et al. | |
| 7,918,793 B2 | 4/2011 | Altmann et al. | |
| 7,952,718 B2 | 5/2011 | Li et al. | |
| 8,145,293 B2 | 3/2012 | Zhang et al. | |
| 8,208,995 B2 | 6/2012 | Tearney et al. | |
| 8,289,522 B2 | 10/2012 | Tearney et al. | |
| 8,412,312 B2 | 4/2013 | Judell et al. | |
| 8,676,013 B2 | 3/2014 | Bouma et al. | |
| 8,792,757 B2 | 7/2014 | Boudoux et al. | |
| 8,928,889 B2 | 1/2015 | Tearney et al. | |
| 9,087,368 B2 | 7/2015 | Tearney et al. | |
| 9,254,102 B2 | 2/2016 | Tearney et al. | |
| 9,295,391 B1 | 3/2016 | Tearney et al. | |
| 9,332,942 B2 | 5/2016 | Jaffer et al. | |
| 9,526,424 B2 | 12/2016 | Judell et al. | |
| 9,557,154 B2 | 1/2017 | Tearney et al. | |
| 9,610,064 B2 | 4/2017 | Adler et al. | |
| 9,646,377 B2 | 5/2017 | Tearney et al. | |
| 9,713,488 B2 | 7/2017 | Hutchinson | |
| 9,763,623 B2 | 9/2017 | Tearney et al. | |
| 9,907,527 B2 * | 3/2018 | Dascal .................. | A61B 6/504 |
| 9,907,536 B2 | 3/2018 | Courtney et al. | |
| 10,109,058 B2 * | 10/2018 | Ambwani ............... | G06T 7/174 |
| 10,130,259 B2 | 11/2018 | Lam et al. | |
| 10,285,568 B2 | 5/2019 | Teamney et al. | |
| 10,675,003 B2 | 6/2020 | Hiltner et al. | |
| 10,743,749 B2 | 8/2020 | Yamada | |
| 10,895,692 B2 | 1/2021 | Yamada | |
| 10,912,462 B2 | 2/2021 | Wang et al. | |
| 2009/0234231 A1 | 9/2009 | Knight et al. | |
| 2010/0092389 A1 | 4/2010 | Jaffer | |
| 2011/0019058 A1 | 1/2011 | Sakai et al. | |
| 2011/0071405 A1 | 3/2011 | Judell et al. | |
| 2011/0292400 A1 | 12/2011 | Fleming et al. | |
| 2011/0299091 A1 | 12/2011 | Yun et al. | |
| 2012/0022360 A1* | 1/2012 | Kemp ................... | A61B 5/1459 600/407 |
| 2012/0101374 A1 | 4/2012 | Tearney et al. | |
| 2014/0180083 A1* | 6/2014 | Hoseit ................. | A61B 5/0084 600/431 |
| 2014/0180133 A1 | 6/2014 | Brennan et al. | |
| 2014/0187963 A1 | 7/2014 | Corl | |
| 2014/0276011 A1 | 9/2014 | Schmitt et al. | |
| 2015/0213629 A1 | 7/2015 | Celi et al. | |
| 2016/0228071 A1* | 8/2016 | Wang ..................... | A61B 5/339 |
| 2016/0228097 A1 | 8/2016 | Jaffer et al. | |
| 2017/0135584 A1 | 5/2017 | Tearney et al. | |
| 2018/0003481 A1 | 1/2018 | Yamada et al. | |
| 2018/0045501 A1 | 2/2018 | Elmaanoui | |
| 2019/0059734 A1 | 2/2019 | Yamada | |
| 2019/0083062 A1* | 3/2019 | Barone .............. | A61B 1/00096 |
| 2019/0105015 A1 | 4/2019 | Stigall et al. | |
| 2019/0298174 A1 | 10/2019 | Watanabe | |
| 2019/0374109 A1 | 12/2019 | Wu et al. | |
| 2020/0013164 A1 | 1/2020 | Elmaanaoui | |
| 2020/0046283 A1 | 2/2020 | Tearney et al. | |
| 2020/0126195 A1 | 4/2020 | Elmaanaoui | |
| 2020/0390323 A1 | 12/2020 | Yamada | |
| 2021/0077037 A1 | 3/2021 | Kunio | |
| 2021/0121132 A1 | 4/2021 | Watanabe et al. | |
| 2021/0174125 A1 | 6/2021 | Zhang | |
| 2021/0407098 A1 | 12/2021 | Athanasiou | |
| 2022/0040402 A1 | 2/2022 | Elmaanaoui | |
| 2022/0044428 A1 | 2/2022 | Elmaanaoui et al. | |
| 2023/0015390 A1 | 1/2023 | Elmaanaoui | |

FOREIGN PATENT DOCUMENTS

| | | |
|---|---|---|
| WO | 2016/015052 A1 | 1/2016 |
| WO | 2016/144878 A1 | 9/2016 |
| WO | 2016/182164 A1 | 11/2016 |

OTHER PUBLICATIONS

Sudhir Rathore,"Association of coronary plaque composition and arterial remodelling: A optical coherence tomography study," Oct. 20, 2011, Atherosclerosis 221 (2012) 405-415,SciVerse ScienceDirect, pp. 405-413.*

Matheus Cardoso Moraes,"Automatic lumen segmentation in IVOCT images using binary morphological reconstruction," Aug. 9, 2013,BioMedical Engineering OnLine vol. 12, Article No. 78 (20130, pp. 1-14.*

Sean M. O'Malley,"Image-Based Gating of Intravascular Ultrasound Pullback Sequences," May 7, 2008, IEEE Transactions on Information Technology in Biomedicine, vol. 12, No. 3, May 2008,pp. 299-303.*

Loretta Scolaro,"Molecular imaging needles: dual-modality optical coherence tomography and fluorescence imaging of labeled antibodies deep in tissue," Apr. 21, 2015,Biomedical Optics Express,May 1, 2015, vol. 6, No. 5,pp. 5-14.*

Claudio Chiastra,"Patient-Specific Modeling of Stented Coronary Arteries Reconstructed from Optical Coherence Tomography: Towards a Widespread Clinical Use of Fluid Dynamics Analyses," Dec. 27, 2017,Journal of Cardiovascular Translational Research (2018) 11,pp. 157-167.*

Jianping Su,"Real-time swept source optical coherence tomography imaging of the human airway using a microelectromechanical system endoscope and digital signal processor," Jul. 1, 2008, Journal of Biomedical Optics vol. 13( 3) , pp. 030506-1-030506-3.*

Su, J., et al., "Real-time swept source optical coherence tomography imaging of the human airway using a microelectromechanical system endoscope and digital signal processor", J. Biomed. Opt., vol. 13, No. 3, May-Jun. 2008, pp. 1-8.

Hariri, L.P., et al., "An automatic image processing algorithm for initiating and terminating intracoronary OFDI pullback", Biomed. Opt. Express, vol. 1, No. 2, Sep. 1, 2010, pp. 566-573.

Lanzer, P., "Catheter-Based Cardiovascular Interventions: A Knowledge-Based Approach", First Published: Jul. 2012, p. 364.

Volcano, Volcano Revo Option, Operator's Manual, Software Version Level 3.3.X, Nov. 2012, pp. 1-22.

Kashiwagi, M., et al., "Optical Coherence Tomography in Coronary Artery Disease: Toward Sub cellular Imaging", Austin J. Clin. Cardiolog., vol. 1, No. 3, Apr. 2014, pp. 1019-1022.

Suter, M. J., et al., "Optimizing flushing parameters in intracoronary optical coherence tomography: an in vivo swine study", Int. J. Cardiovasc. Imaging, vol. 31, Apr. 2015, pp. 1097-1106.

Scolaro, L., et al., "Molecular imaging needles: dual-modality optical coherence tomography and fluorescence maging of labeled antibodies deep in tissue", Biomed. Opt. Express, vol. 6, No. 5, May 1, 2015, pp. 1767-1781.

Matheus Cardoso Moraes, et al., "Automatic lumen segmentation in IVOCT images using binary morphological reconstruction", BioMedical Engineering OnLine, BioMed Central Ltd., vol. 12, 78, Aug. 2013, pp. 1-17, https://doi.org/10.1186/1475-925X-12-78 (17 pages in PDF file).

Hariri, Lida P., et al., "An automatic image processing algorithm for initiating and terminating intracoronary OFDI pullback", Biomedical Optics Express, vol. 1., No. 2, Sep. 1, 2010, pp. 566-573, obtained at https://pubmed.ncbi.nlm.nih.gov/21258490/.

(56) References Cited

OTHER PUBLICATIONS

Nobuyuki Otsu, "A Threshold Selection Method from Gray-Level Histograms", IEEE Transactions on Systems, Man, and Cybernetics, vol. SMC-9, No. 1, Jan. 1979, pp. 62-66.
Tyler Andrews, "Computation Time Comparison Between Matlab and C++ Using Launch Windows", American Institute of Aeronautics and Astronautics, California Polytechnic State University San Luis Obispo, Aerosp. Eng., Jun. 2012., pp. 1-6.

* cited by examiner

| Date | Filename | System | Catheter | Media | Injection |
|---|---|---|---|---|---|
| October 31, 2017 | 20171031_00004882_00003_00001 | System 1 | Catheter 1 | Contrast | Manual |
| October 31, 2017 | 20171031_00004882_00003_00008 | System 1 | Catheter 1 | Contrast | Automatic (4ml/s, 12ml) |
| October 31, 2017 | 20171031_00004882_00004_00010 | System 1 | Catheter 1 | Contrast | Automatic (4ml/s, 12ml) |
| October 31, 2017 | 20171031_00004882_00005_00004 | System 1 | Catheter 2 | Contrast | Automatic (4ml/s, 12ml) |
| October 31, 2017 | 20171031_00004882_00005_00008 | System 1 | Catheter 2 | Contrast | Automatic (4ml/s, 12ml) |
| October 31, 2017 | 20171031_00004882_00006_00005 | System 1 | Catheter 2 | Contrast | Automatic (4ml/s, 12ml) |
| March 5, 2019 | 50735_20190305_112658_PrePullback | System 2 | Catheter 3 | Contrast | Automatic (3ml/s, 10ml) |
| March 5, 2019 | 50735_20190305_113142_PrePullback | System 2 | Catheter 3 | Saline | Manual (10ml) |
| March 5, 2019 | 50735_20190305_114604_PrePullback | System 2 | Catheter 3 | Contrast | Automatic (3ml/s, 10ml) |
| March 5, 2019 | 50735_20190305_120328_PrePullback | System 2 | Catheter 3 | Contrast | Automatic (3ml/s, 10ml) |
| March 5, 2019 | 50735_20190305_121333_PrePullback | System 2 | Catheter 3 | Contrast | Automatic (3ml/s, 10ml) |
| March 5, 2019 | 50735_20190305_122657_PrePullback | System 2 | Catheter 3 | Contrast | Automatic (3ml/s, 10ml) |
| March 5, 2019 | 50735_20190305_123739_PrePullback | System 2 | Catheter 3 | Contrast | Automatic (3ml/s, 10ml) |
| March 5, 2019 | 50735_20190305_124854_PrePullback | System 2 | Catheter 3 | Contrast | Automatic (3ml/s, 10ml) |
| March 5, 2019 | 50735_20190305_125659_PrePullback | System 2 | Catheter 3 | Contrast | Automatic (3ml/s, 10ml) |
| March 5, 2019 | 50735_20190305_131511_PrePullback | System 2 | Catheter 4 | Contrast | Automatic (3ml/s, 10ml) |
| March 5, 2019 | 50735_20190305_131628_PrePullback | System 2 | Catheter 4 | Contrast | Automatic (3ml/s, 10ml) |

FIG. 13

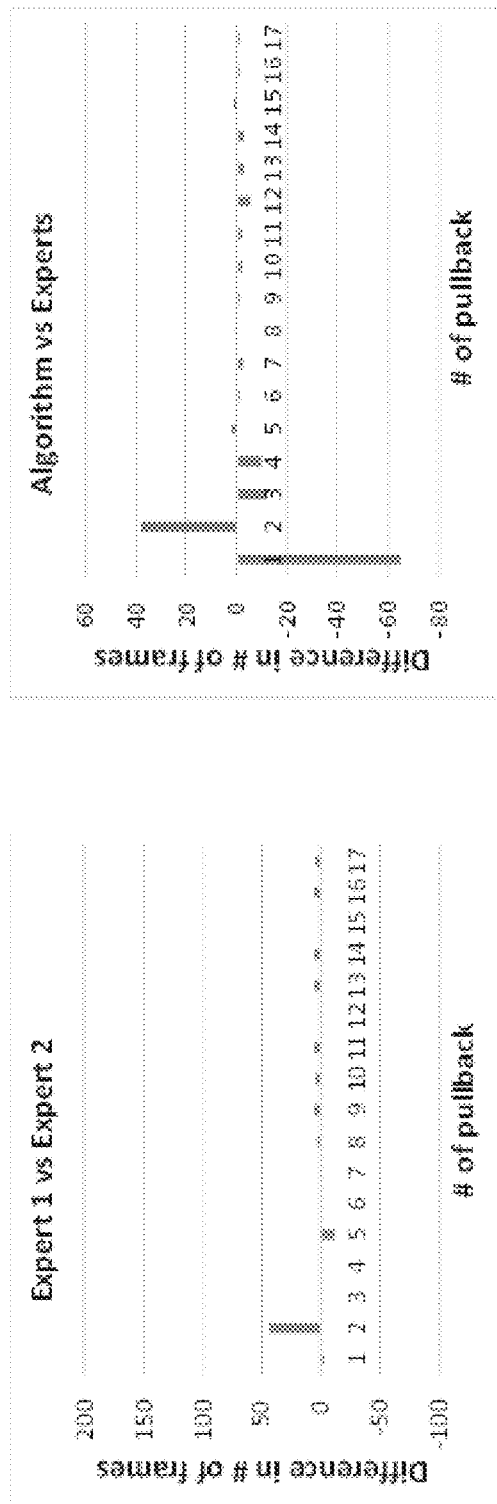
FIG. 14A
FIG. 14B
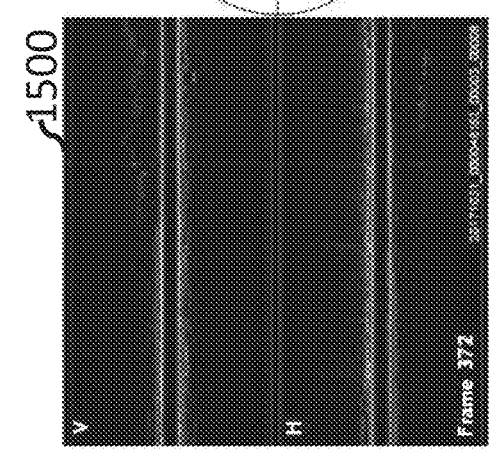
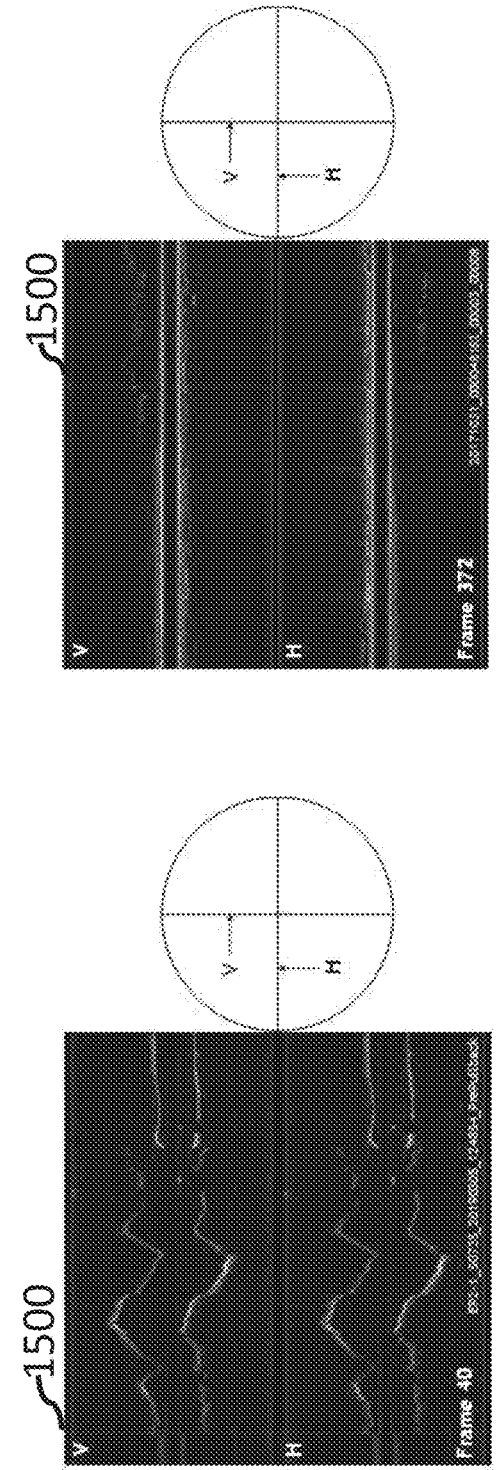
FIG. 15A
FIG. 15B

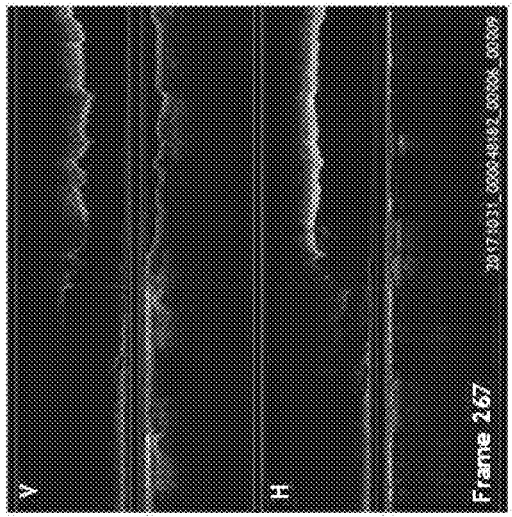
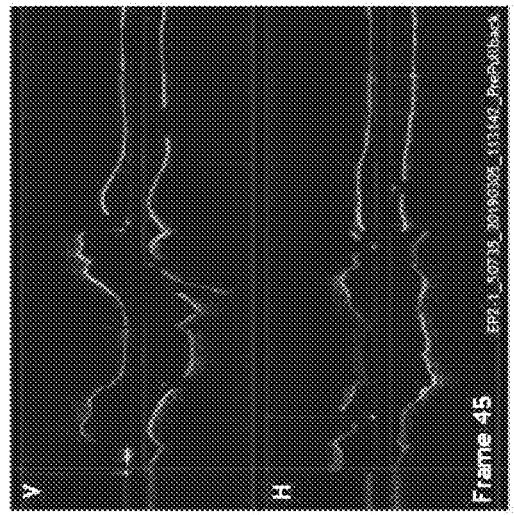
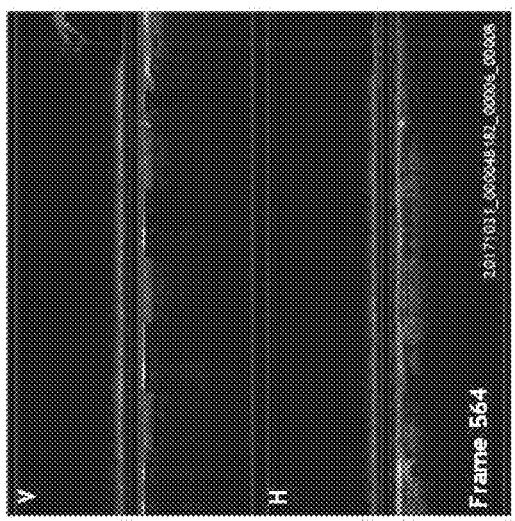
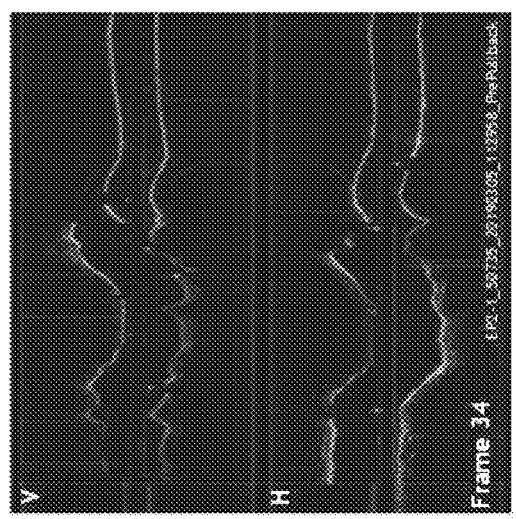
FIG. 16E
FIG. 16F
FIG. 16G
FIG. 16H

AUTO-PULLBACK TRIGGERING METHOD FOR INTRACORONARY IMAGING APPARATUSES OR SYSTEMS USING BLOOD CLEARING

CROSS-REFERENCE TO RELATED APPLICATION(S)

This application relates, and claims priority, to U.S. Patent Application Ser. No. 63/062,300, filed Aug. 6, 2020, the entire disclosure of which is incorporated by reference herein in its entirety.

FIELD OF THE INVENTION

This present disclosure generally relates to computer imaging and/or to the field of optical imaging, particularly to devices, systems, methods, and storage mediums for using multiple imaging modalities, such as, but not limited to, Optical Coherence Tomography (OCT), Multi-mode OCT (MMO-OCT), near-infrared fluorescence (NIRAF), etc. Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for performing auto-pullback triggering are discussed herein.

BACKGROUND OF THE INVENTION

Optical coherence tomography (OCT) is an imaging modality that was introduced as the method of choice for high resolution intracoronary imaging. The concept of the technology is similar to the intracoronary ultrasound but instead of measuring the backscattered acoustic signals it measures the delay of backscattered light. However, since light cannot penetrate soft tissue and blood, blood flushing using radiographic contrast agents is required. Blood flushing occurs before the pullback starts and needs to be controlled by well-trained and experienced experts.

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery. As such, OCT may be used for high resolution intracoronary imaging.

OCT is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

OCT measures the delay of backscattered light. However, since light cannot penetrate soft tissue and blood, blood flushing using radiographic contrast agents may be used. Blood flushing occurs before the pullback starts and is controlled by well-trained and experienced experts. Since the OCT pullback speed is extremely fast (~2 sec/~62:100 mm pullback), it is crucial for the pullback to start immediately when the blood is cleared in order to guarantee the imaging of the whole targeted vessel. Frequently, an unsynchronized flushing-pullback results in imaging loss of a vessel's part, and a second pullback may be needed. Moreover, since the blood clearing contrast agents have to be under a specific dosage level, a possible second pullback needed due to a first unsynchronized flushing may be harmful or pose clinical risk to the patient, and may be burdensome to a physician or other expert clinician. Therefore, a method was introduced, which detects the absence of blood and triggers an automatic pullback. However, this method is complicated (e.g., involves a number of parameters which should be modified by a user to adjust the behavior of a flush clearing state) and requires the user to update different threshold values.

As such, there is a need for a method that detects a clearing state of blood in a vessel or target area and that automatically triggers a pullback without any user interaction. Indeed, there is a need to provide reliable, efficient measurements for the whole OCT pullback.

Accordingly, it would be desirable to provide at least one imaging or optical device, system, method, and storage medium for using, controlling, and/or emphasizing one or more multiple imaging modalities, for example, by using a method or methods that trigger an automatic pullback using blood clearing, and/or that provide reliable and efficient measurements and imaging for the whole OCT pullback.

SUMMARY OF THE INVENTION

Accordingly, it is a broad object of the present disclosure to provide imaging (e.g., OCT, NIRAF, etc.) apparatuses, systems, methods and storage mediums for using and/or controlling an auto-pullback triggering method using blood clearing in one or more apparatuses or systems (e.g., an intracoronary imaging apparatus or system). It is also a broad object of the present disclosure to provide OCT devices, systems, methods and storage mediums using an interference optical system, such as an interferometer (e.g., SD-OCT, SS-OCT, MM-OCT, etc.).

In one or more embodiments, at least one method may detect a clearing state of blood in a target object, sample, or area (e.g., a vessel) and may automatically trigger the pullback (e.g., without any user interaction, does not require user interaction, etc.). As such, in one or more embodiments a whole targeted object, sample, or area (e.g., a vessel) may be imaged minimizing the contrast overdosing risk (e.g., radiographic contrast overdose is reduced, avoided, or minimized by limiting, minimizing, or avoiding the use of a contrast agent).

One or more embodiment of the present disclosure overcomes the aforementioned issues and provides an auto-pullback method(s) which does/do not require user interaction. One or more auto-pullback method embodiments may include: (a) importing a plurality of A-lines, an image, or images; (b) initializing a counter; (c) segmenting the A-lines, the image, or the images; (d) separating the segmented A-lines, image, or images into three or more equal parts; (e) defining a Blood Imaging Area (BIA), which is an area surrounding an imaging probe in a case where blood is present; (f) detecting a number of objects within the BIA within a first frame of the segmented A-lines, image, or images; (g) perform a counting step: in a case where the number of the objects is less than N, wherein N is a minimum acceptance number of objects that define a partial cleared or cleared state, then increase the counter by a set or predetermined amount or by 1, and in a case where the number of objects is N or more, then repeat steps (c)-(g) with a second or subsequent frame; and (h) ending a signal to trigger pullback when the counter is X or greater, wherein X is a predetermined value. One or more additional auto-pullback method embodiments may include: (i) importing A-lines (polar image) of a current frame in a scan mode (e.g., for a full speed spinning catheter or probe), preparing the frame for the next step by deleting the catheter or probe and extravascular noise, and setting a counter to zero; (ii) segmenting each image using automatic thresholding, and separating the image into four equal parts which correspond to four Cartesian quadrants; (iii) deleting any detected object (e.g., a small object, an object of a predetermined size, etc.), which might correspond to noise, residual blood, or other artifacts, and counting how many objects overlap with the Blood Imaging Area (BIA) (also referred to as a Blood Imaging Depth (BID) area). BIA is defined or denoted as the area above a specific distance from the catheter tip predefined using images with blood presence; (iv) if at least three (3) objects are not overlapping with BIA, then increasing the counter to one; if not, moving to the next frame; and (v) when the counter is equal to three, five, etc. (or another predetermined or set number), then triggering the automatic pullback.

One or more embodiments may provide one or more of the following advantages or benefits: (i) By dividing an image to three or more (e.g., four) parts/quadrants and studying the flushing state in each part, the method ensures that the flushing state may be detected even in small diameter vessels (for example, when the diameter of the vessel is small, there is a difficulty in discriminating between blood, lumen, and catheter or probe objects (the catheter or probe often may be touching a wall of a lumen or vessel); (ii) By applying a counter in at least one method embodiment, optimal pullback flushing synchronization may be achieved (for example, sequential frames may be detected as clear before the pullback starts avoiding imaging loss); and/or (iii) By applying one or more features of the present disclosure, no user interaction is needed, or may be optional, since automatic thresholding is performed.

One or more embodiments of the present disclosure may involve a method for triggering an automatic pullback during imaging (e.g., intravascular imaging), and may include the following: synchronizing the flushing and catheter or probe pullback states in imaging (e.g., OCT imaging); reducing or minimizing the medical experts tasks during intravascular imaging; reducing or minimizing the pullback imaging loss caused by late or early pullback triggering; and preventing the use of or avoiding a second flushing such that risk to a patient is reduced or minimized.

In one or more embodiments, a cleared lumen state may be detected in three or more or four parts/quadrants. In one or more embodiments, the flushing state may be detected even in small diameter vessels. Detecting moving binary objects of the four quadrants in small diameter vessels is more robust than comparing radiuses/rings, which may be very close due to a small artery diameter.

One or more embodiments may incorporate a counter. Measuring how many frames in a row have a blood clear state is at least one way to ensure that optimal pullback-flushing synchronization is achieved. The counter achieves a feature where a same or similar clearance state is in consecutive frames in one or more embodiments.

In one or more embodiments having no user interaction, one or more methods thereof do not require any parameter(s) to be modified by the user to adjust the behavior of the flush clearing state (e.g., when the algorithm or method fails). Indeed, reducing or avoiding user interaction improves efficiency and reduces error(s).

In one or more embodiments, one or more A-lines and/or real-time lumen distance calculations may be processed as discussed in U.S. Pat. App. No. 63/046,495, filed on Jun. 30, 2020, which is incorporated by reference herein in its entirety.

Lumen edge detection in OCT imaging may be susceptible to artifacts, which correspond to many features, including, but not limited to: stent strut(s), guide wire(s), image brightness variation due to imaging angle, sheath reflections, an irregular shape of a vessel cross section, etc. Certain applications of OCT, such as multimodality OCT (MMOCT) systems/apparatuses, may use lumen edge detection to correct near-infrared autofluorescence (NIRAF) or near-infrared fluorescence (NIRF) signal distance attenuation. Preferably, accurate, real-time NIRAF or NIRF imaging uses accurate detection of lumen edge(s) in real-time based on a single frame of an OCT image. See, for example, U.S. Pat. Pub. 2019/0298174, U.S. patent application Ser. No. 16/131, 662, and U.S. Pat. Appl. Ser. No. 62/925,655, each of which are herein incorporated by reference in their entireties. Accurately detecting a lumen edge(s) using a single OCT frame helps to improve overall object or target, such as a vessel, measurement accuracy, including for post processing.

The present disclosure describes a means to allow OCT users to focus on the area of interest and/or to perform auto-pullback triggering in all imaging modalities, such as, but not limited to, a tomography image, near-infrared fluorescence (NIRAF) information in carpet view, three-dimensional (3D) rendering of a coronary vessel in a half pipe display, lumen diameter display, longitudinal view, and angiography view. This allows the users to get a full view of the structural vessel information using one modality or multi-modalities and allows configurability of the function for more targeted focus when providing the fast, efficient A-line lumen segmentation method(s).

In accordance with one or more embodiments of the present disclosure, apparatuses and systems, and methods and storage mediums for auto-pullback triggering may operate to characterize biological objects, such as, but not limited to, blood, mucus, tissue, etc.

It should be noted that one or more embodiments of the auto-pullback triggering method(s) of the present disclosure may be used in other imaging systems, apparatuses or devices, where images are formed from signal reflection and scattering within tissue sample(s) using a scanning probe. For example, IVUS images may be processed in addition to or instead of OCT images.

One or more embodiments of the present disclosure may be used in clinical application(s), such as, but not limited to, intervascular imaging, intravascular imaging, atherosclerotic plaque assessment, cardiac stent evaluation, intracoronary imaging using blood clearing, balloon sinuplasty, sinus stenting, arthroscopy, ophthalmology, ear research, veterinary use and research, etc.

In accordance with at least another aspect of the present disclosure, one or more technique(s) discussed herein may be employed as or along with features to reduce the cost of at least one of manufacture and maintenance of the one or more apparatuses, devices, systems and storage mediums by reducing or minimizing a number of optical and/or processing components and by virtue of the efficient techniques to cut down cost of use/manufacture of such apparatuses, devices, systems and storage mediums.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 13 is a summary of the MMOCT pullbacks used in the experiments performed in accordance with one or more aspects of the present disclosure;

FIGS. 14A-14B include graphs showing the difference between results (difference in number of frames against the number of pullbacks) obtained by expert 1 and expert 2 in experiments conducted (FIG. 14A) and the difference between the algorithm or method embodiment used and the experts (FIG. 14B) in accordance with one or more aspects of the present disclosure;

FIGS. 15A-15B include graphs and respective longitudinal views showing embodiment examples of qualitative assessment of at least one embodiment of an auto-pullback method or algorithm in two different pullbacks in accordance with one or more aspects of the present disclosure;

DETAILED DESCRIPTION OF THE PRESENT INVENTION

Figure 1:
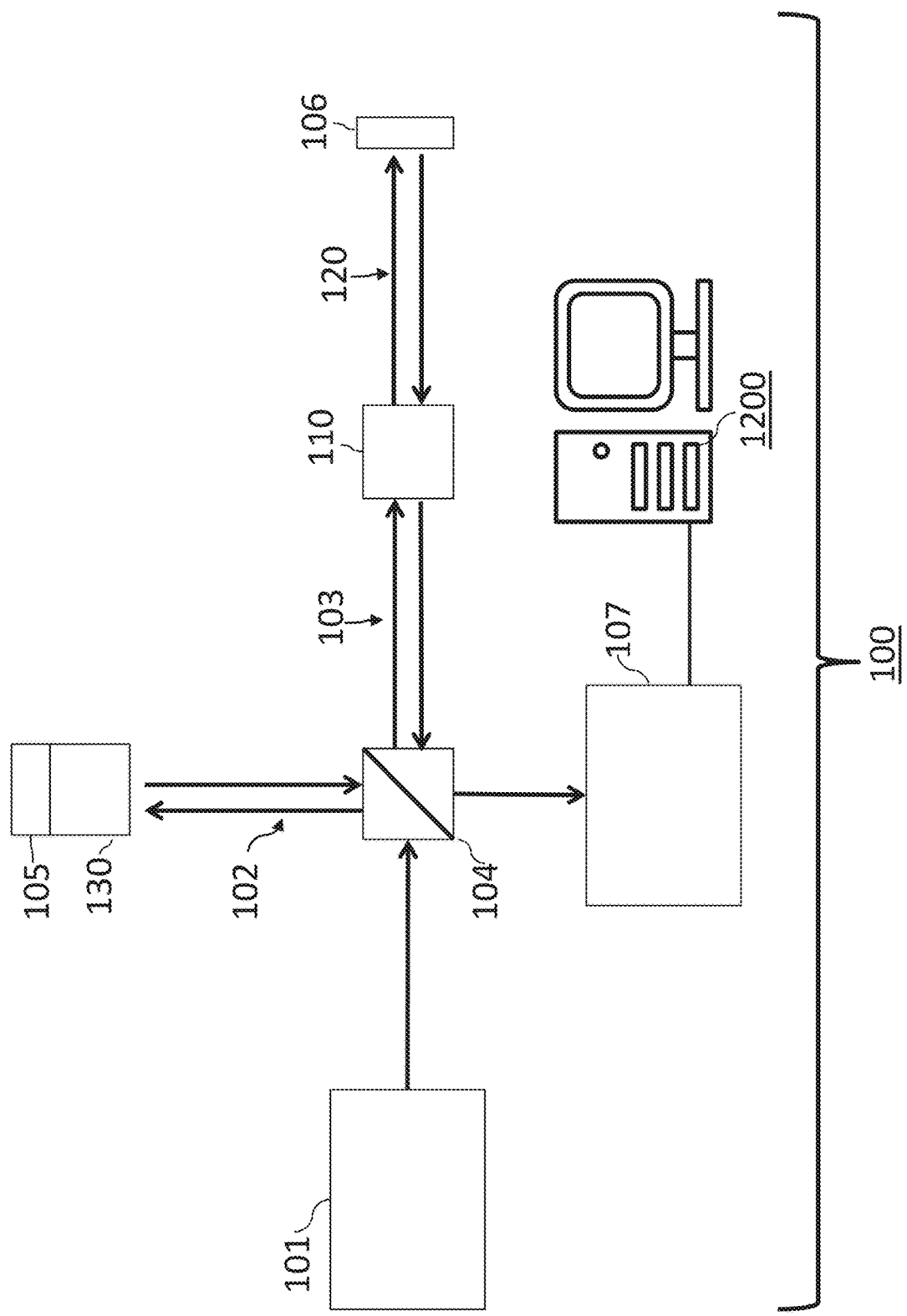
FIG. 1 is a schematic diagram showing at least one embodiment of a system that may be used for performing one or more embodiments of a real-time lumen distance calculation method(s) based on 3D A-line signal data in accordance with one or more aspects of the present disclosure.

One or more devices, systems, methods and storage mediums for characterizing tissue, or an object or sample, using one or more imaging and/or calculation techniques or modalities (such as, but not limited to, OCT, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1 through 23.

In one or more embodiments, at least one method may detect a clearing state of blood in a target object, sample, or area (e.g., a vessel) and may automatically trigger the pullback (e.g., without any user interaction, does not require user interaction, etc.). As such, in one or more embodiments a whole targeted object, sample, or area (e.g., a vessel) may be imaged minimizing the contrast overdosing risk (e.g., radiographic contrast overdose is reduced, avoided, or minimized).

One or more embodiments of the present disclosure may involve a method for triggering an automatic pullback during imaging (e.g., intravascular imaging), and may include the following: synchronizing the flushing and catheter or probe pullback states in imaging (e.g., OCT imaging); reducing or minimizing the medical experts tasks during intravascular imaging; reducing or minimizing the pullback imaging loss caused by late or early pullback triggering; and preventing the use of or avoiding a second flushing such that risk to a patient is reduced or minimized.

One or more embodiments may provide one or more of the following advantages or benefits: (i) By dividing an image to four parts/quadrants and studying the flushing state in each part, the method ensures that the flushing state may be detected even in small diameter vessels (for example, when the diameter of the vessel is small, there is a difficulty in discriminating between blood, lumen, and catheter or probe objects (the catheter or probe often may be touching a wall of a lumen or vessel); (ii) By applying a counter in at least one method embodiment, optimal pullback flushing synchronization may be achieved (for example, sequential frames may be detected as clear before the pullback starts avoiding imaging loss); and/or (iii) By applying one or more features of the present disclosure, no user interaction is needed, or may be optional, since automatic thresholding is performed.

One or more embodiments of the present disclosure may overcome the aforementioned issues and may provide an auto-pullback method(s), which does/do not require user interaction. One or more auto-pullback method embodiments may include: (i) importing A-lines (polar image) of a current frame in a scan mode (e.g., for a full speed spinning catheter or probe), preparing the frame for the next step by deleting the catheter or probe and extravascular noise, and setting a counter to zero; (ii) segmenting each image using automatic thresholding, and separating the image into four equal parts which correspond to four Cartesian quadrants; (iii) deleting any detected object (e.g., a small object, an object of a predetermined size, etc.), which might correspond to noise, residual blood, or other artifacts, and counting how many objects overlap with the Blood Imaging Area (BIA). BIA may be denoted or defined as the area above a specific distance from the catheter tip predefined by using images with blood presence; (iv) if at least three (3) objects are not overlapping with BIA, then increasing the counter to or by one; if not, moving to the next frame; and (v) when the counter is equal to three, five, etc. (or another predetermined or set number), then triggering the automatic pullback.

In one or more embodiments, a cleared lumen state may be detected in four parts/quadrants. In one or more embodiments, the flushing state may be detected even in small diameter vessels. Detecting moving binary objects of the four quadrants in small diameter vessels is more robust than comparing radiuses/rings, which may be very close due to a small artery diameter.

One or more embodiments may incorporate a counter. Measuring how many frames in a row have a blood clear state is at least one way to ensure that optimal pullback-flushing synchronization is achieved. The counter guarantees that a same or similar clearance state is in consecutive frames in one or more embodiments.

In one or more embodiments having no user interaction, one or more methods thereof do not require any parameter(s) to be modified by the user to adjust the behavior of the flush clearing state (e.g., when the algorithm or method fails). Indeed, reducing or avoiding user interaction improves efficiency and reduces error(s).

Intravascular optical coherence tomography (IV-OCT) is an imaging technique used to image the surface and partly the arterial wall of the human arteries. IV-OCT measures the delay of the backscattered light in order to image the artery. OCT is commonly used in interventional cardiology and is becoming the method of choice for many applications, including, but not limited to, imaging coronary artery disease. To image the coronaries, a catheter or probe (e.g., the catheter or probe 120) may be inserted through the femoral artery and, using a guide wire, the catheter or probe may be placed inside the targeted coronary. The catheter or probe (e.g., the catheter or probe 120) may spin around itself emitting light, and then a pullback along the targeted vessel or other target, object, or sample (e.g., the target, object, or sample 106) may be performed. During the pullback of the catheter or probe (e.g., the catheter or probe 120), the reflected optical signals may be stored (e.g., A-line images (e.g., an OCT image in polar coordinates, an image in polar coordinates, an image of a particular imaging modality in polar coordinates, etc.)), transformed to Cartesian coordinates (2D OCT frame), and shown to the user and/or displayed on a display screen Turning now to the details of the figures, processing intravascular imaging data and/or performing auto-pullback triggering method(s) may be performed in one or more ways as discussed herein. One or more displays discussed herein may allow a user of the one or more displays to use, control and/or emphasize one or more imaging and/or calculation techniques or modalities, such as, but not limited to, OCT, NIRAF, etc., and may allow the user to use, control, and/or emphasize the one or more imaging techniques or modalities synchronously, and/or may allow the user to perform auto-pullback triggering method(s) (including method(s) involving blood clearing) and/or to process intravascular imaging data.

As shown diagrammatically in FIG. 1, one or more embodiments of a system or apparatus for visualizing, emphasizing and/or controlling one or more imaging modalities, and/or for performing auto-pullback triggering method(s) (including method(s) involving blood clearing) and/or to process intravascular imaging data, of the present disclosure may be involved with one or more predetermined or desired procedures, such as, but not limited to, medical procedure planning and performance.

FIG. 1 shows an OCT system 100 (as referred to herein as "system 100" or "the system 100") which operates to utilize an OCT technique, including, but not limited to, one or more embodiments of allowing the user to use, control, and/or emphasize the one or more imaging techniques or modalities synchronously, and/or allowing performance of auto-pullback triggering method(s) (including method(s) involving blood clearing) and/or processing intravascular imaging data techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter or probe 120 (as diagrammatically shown in FIGS. 1-2), and the system 100 may interact with a sample or target 106 (e.g., via the catheter/probe 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104, and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit; also referred to herein as a patient interface component (PIC)) 110 and the catheter or probe 120 in the sample arm 103. Both of the reference and sample beams combine (or recombine) at the splitter 104 and generate interference patterns.

The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 22 or FIG. 23, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100", the system 100''', etc.

In accordance with at least one aspect of the present disclosure, a feature of OCT systems is implemented using fiber optics. As aforementioned, one application of an OCT technique of the present disclosure is to use OCT with a catheter or probe 120 as schematically shown in FIGS. 1-2.

Figure 2:
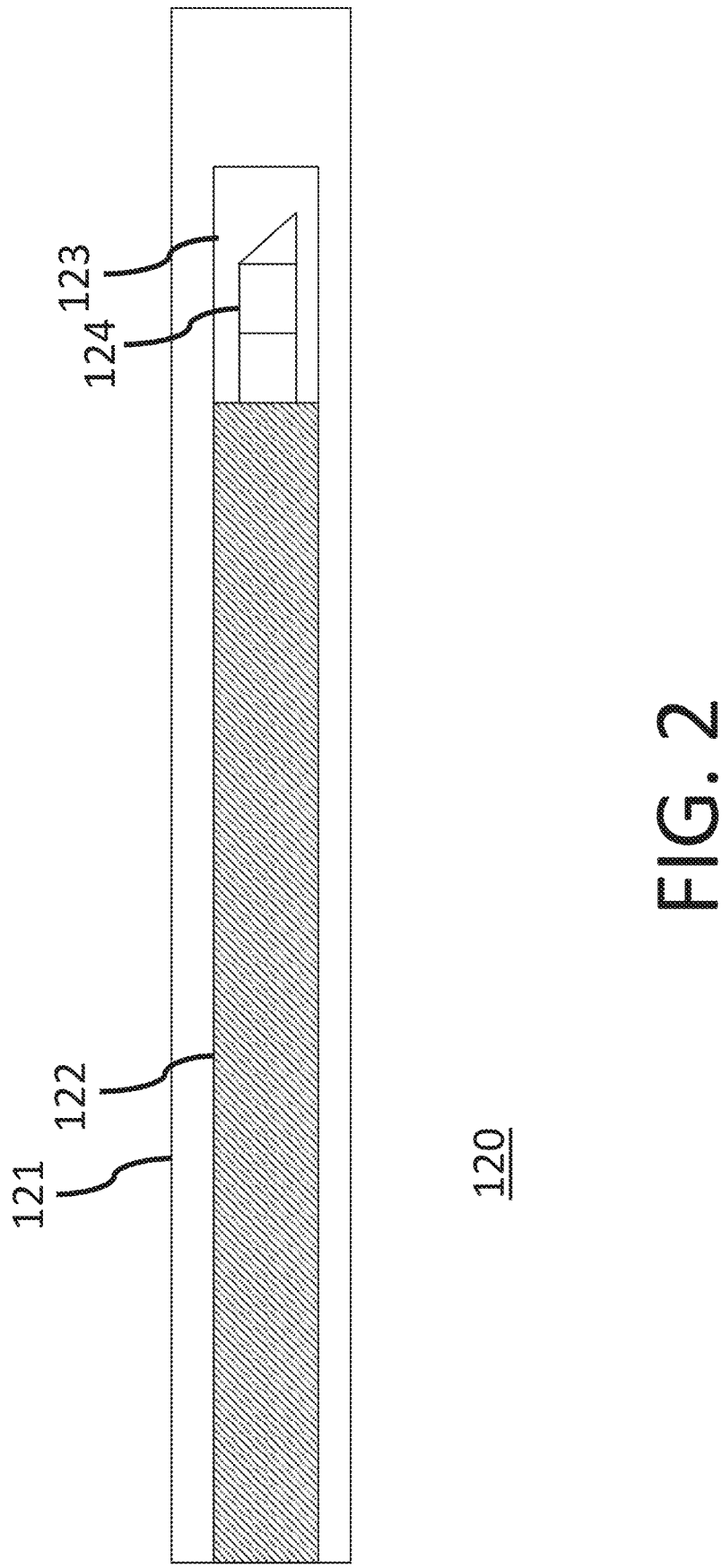
FIG. 2 is a diagram of an embodiment of a catheter or probe that may be used with at least one embodiment of an apparatus, method, or system for performing A-line lumen distance calculation techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2), a needle, a capsule, a patient interface unit or component (e.g., the patient interface unit or component 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 22 and/or the console 1200' of FIG. 23 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100", the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 22 and/or the console 1200' of FIG. 23 as further discussed below). The output of the one or more components of the system 100 (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' (e.g., as shown in FIGS. 1, 18-20, and 22-23). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (mating location).

One or more embodiments of a system for increasing imaging depth range may include: an OCT system; a reference reflection adjusted so that a reflection from a system mating connector is visible in an imaging field of view; and one or more processors that operate to determine if a catheter/probe is mated to the system mating connector.

As aforementioned, OCT measures the delay of backscattered light. However, since light cannot penetrate soft tissue and blood, blood flushing using radiographic contrast agents may be used.

Figure 3:
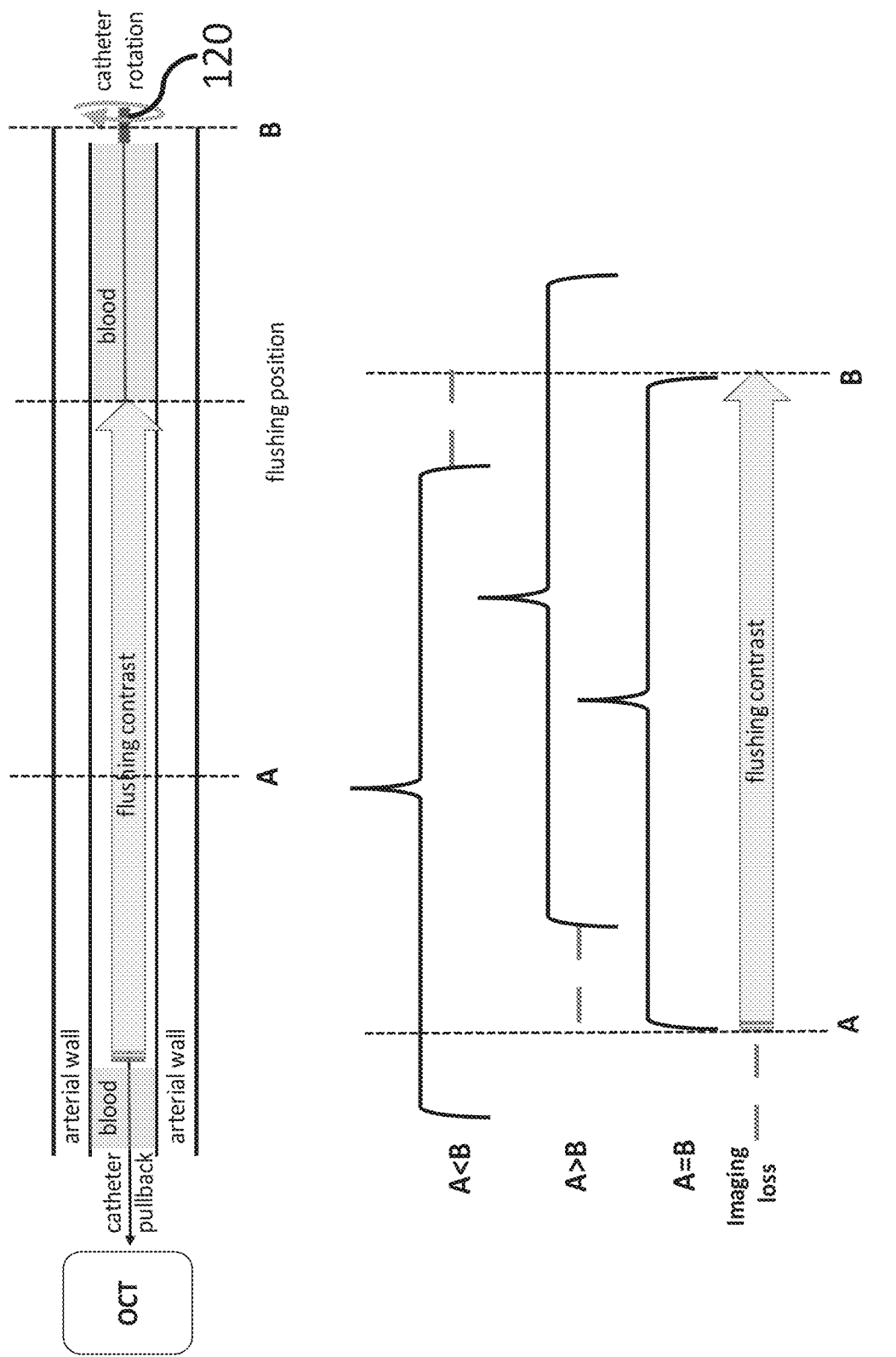
FIG. 3 is a schematic description of at least one embodiment of a flushing a pullback synchronization (points A and B represent the beginning and ending of the targeted segment, respectively) in accordance with one or more aspects of the present disclosure.

In one or more embodiments, the blood clearance state may be synchronized with the catheter pullback to ensure that the whole arterial segment may be imaged. In one or more embodiments where the blood clearance state is not synchronized with a catheter or probe pullback, one or two scenarios may occur: (i) in case of an early pullback, the distal to catheter or probe tip part may not be imaged; and/or (ii) in the case of a late pullback, the proximal part of the catheter or probe may not be imaged in one or more embodiments. A schematic description of the pullback-flushing synchronization issue and the possible imaging loss is shown in FIG. 3 (e.g., where points A and B represent the beginning and ending of a targeted segment, respectively).

Figure 4:
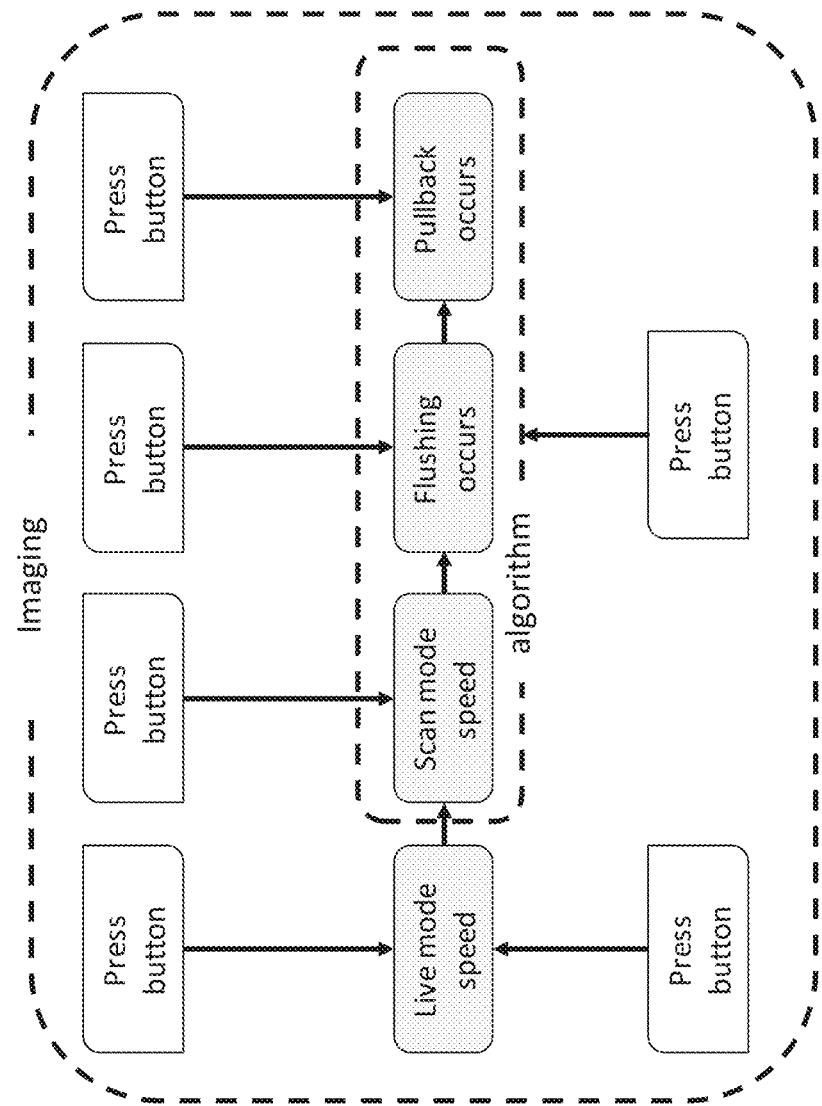
FIG. 4 is a schematic description of at least one embodiment of user tasks before (top of FIG. 4) and after (bottom of FIG. 4) an auto-pullback algorithm or method embodiment example (e.g., the auto-pullback algorithm or method embodiment may integrate three tasks to one to reduce or minimize effort of the user) in accordance with one or more aspects of the present disclosure.
Figure 5:
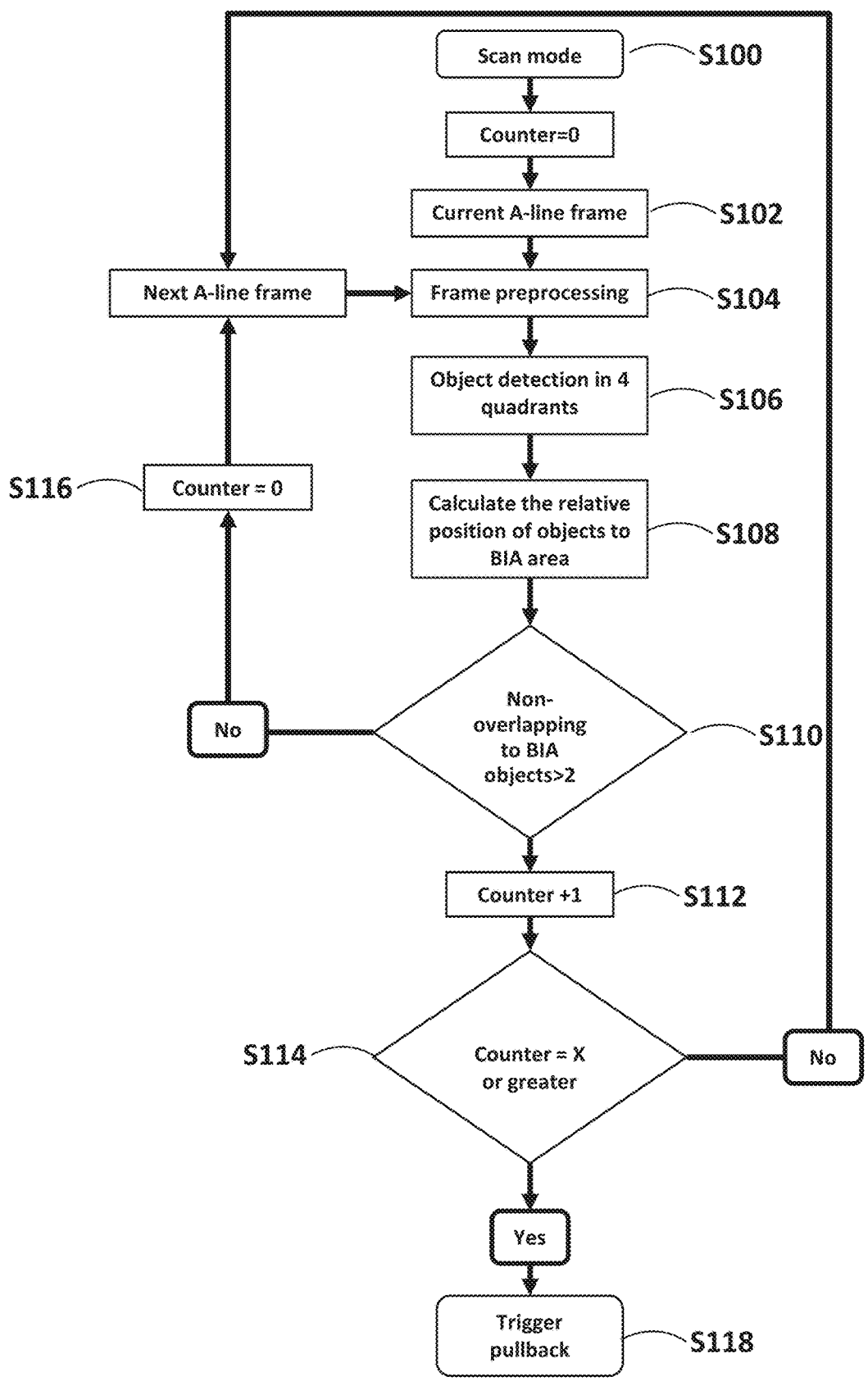
FIG. 5 is a flow diagram of at least one embodiment of an auto-pullback triggering method in accordance with one or more aspects of the present disclosure.

One or more method embodiments of the present disclosure ensures the flushing-pullback synchronization, and minimizes the tasks of a user (e.g., a medical expert, professional, clinician, practitioner, etc.) during the catheterization procedure. As shown in FIG. 4, during intravascular imaging, currently there are four (4) manual tasks required by the user in a serial execution (e.g., pressing four (4) separate buttons to control live mode speed, to control scan mode speed, to cause flushing to occur, to cause pullback to occur, etc.) (see e.g., the user tasks at the top of FIG. 4). One or more method embodiments integrate at least three tasks (e.g., controlling scan mode speed, causing flushing to occur, causing pullback to occur, etc.) to one task (see e.g., the user tasks at the bottom of FIG. 4), reducing or minimizing the user effort. As such, a user does not have to control or update so many variables in one or more methods. For example, a user may push one or two buttons to achieve the four (4) tasks instead of pushing four separate buttons. In one or more embodiments, a user may not have to push a button or otherwise interact with the system or device at all, and the device or system may operate to automatically trigger the pullback without any user interaction.

One or more auto-pullback method embodiments may include: (a) importing a plurality of A-lines, an image, or images; (b) initializing a counter; (c) segmenting the A-lines, the image, or the images; (d) separating the segmented A-lines, image, or images into three or more equal parts; (e) defining a Blood Imaging Area (BIA), which is an area surrounding an imaging probe in a case where blood is present; (f) detecting a number of objects within the BIA within a first frame of the segmented A-lines, image, or images; (g) perform a counting step: in a case where the number of the objects is less than N, wherein N is a minimum acceptance number of objects that define a partial cleared or cleared state, then increase the counter by a set or predetermined amount or by 1, and in a case where the number of objects is N or more, then repeat steps (c)-(g) with a second or subsequent frame; and (h) ending a signal to trigger pullback when the counter is X or greater, wherein X is a predetermined value. Now turning to the details of FIG. 5, at least one embodiment example of an auto-pullback triggering method is shown, and at least one embodiment of an overall workflow of the method may include: (i) importing A-lines (polar image) of a current frame of an image in a scan mode (e.g., for a full speed spinning catheter or probe), preparing the frame for the next step by deleting the catheter or probe and extravascular noise or otherwise perform frame pre-processing, and setting a counter to zero (see e.g., steps S100, S102, and S104, respectively, in FIG. 5); (ii) segmenting the image using automatic thresholding, and separating the image into four equal parts which correspond to four Cartesian quadrants (see e.g., step S106 in FIG. 5); (iii) calculating a relative position of object(s) to a Blood Imaging Area (BIA) area, where the BIA is denoted as the area above a specific distance from the catheter or probe tip (predefined using images with blood presence) (see e.g., step S108 in FIG. 5); (iv) deleting any detected object (e.g., a small object, an object of a predetermined size, etc.), which might correspond to noise, residual blood, or other artifacts, and counting how many objects are above a specific distance from the BIA area or are non-overlapping with the BIA area or counting how many objects overlap with the Blood Imaging Area (BIA) (see e.g., step S110 in FIG. 5); (v) if two (2) or more objects (or greater than two objects) are not overlapping with the BIA, then increasing the counter to one or by one (see e.g., step S112 in FIG. 5); if not, setting the counter again to zero, and/or moving to the next frame (see e.g., step S116 in FIG. 5) to repeat steps S104 through S110; and (vi) when the counter is equal to three, five, etc. (or another predetermined or set number), then triggering the automatic pullback (see e.g., steps S114 and S118 in FIG. 5); otherwise, if the counter is not yet equal to three, five, etc. (or the another predetermined or set number, such as, but not limited to, 1, 2, 4, etc.), then moving to the next A-line frame and repeating steps S104 through S110.

In one or more embodiments, the step of calculating a relative position of object(s) from the catheter or probe (see e.g., step S108 in FIG. 5) may be omitted. In one or more embodiments using the BIA, the BIA is denoted as the area above a specific distance from the catheter or probe tip (predefined using images with blood presence) (see e.g., step S108 as discussed above for FIG. 5).

Figure 6:
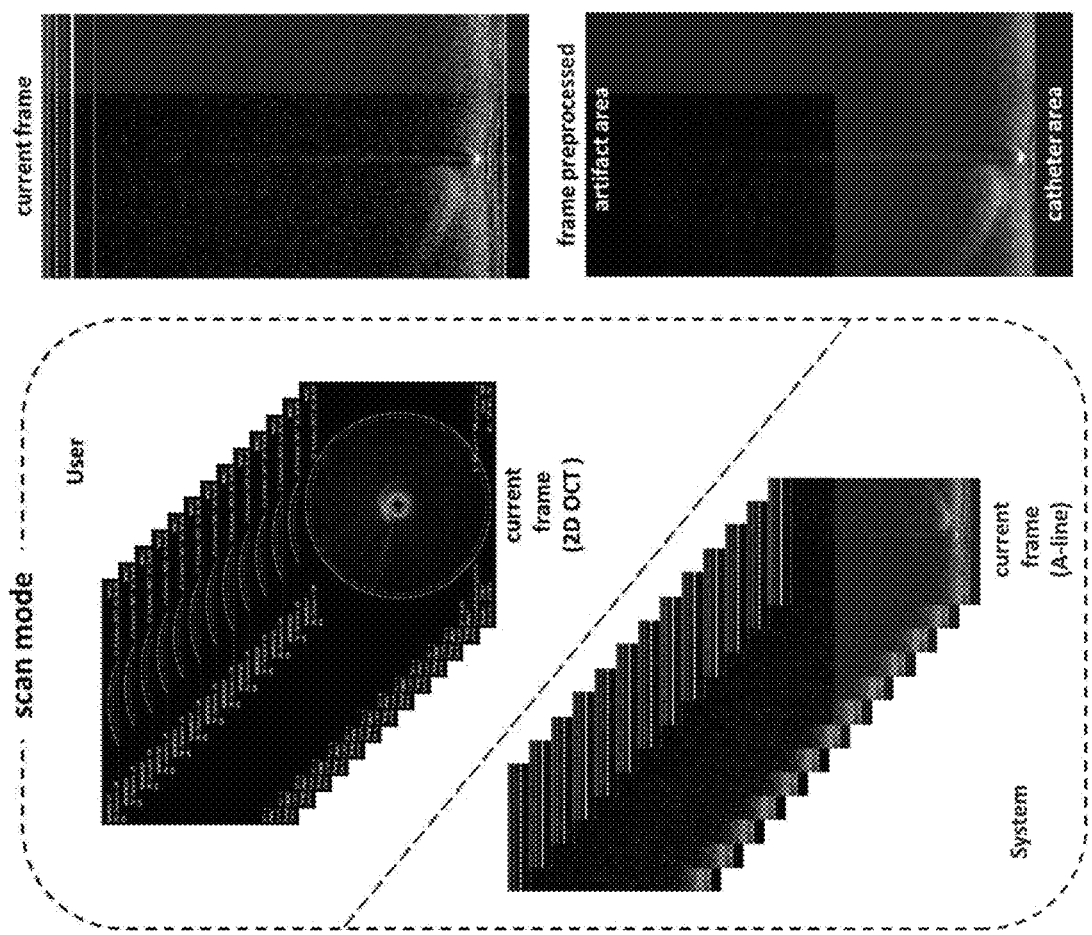
FIG. 6 shows at least one embodiment example of a scan mode setting of an OCT device or system and at least one embodiment of preprocessing of a current frame in accordance with one or more aspects of the present disclosure.

In one or more embodiments, the intracoronary or imaging system (see e.g., step S100) may be set to scan mode (full scanning speed) and a counter may be set to zero. Then, the current block of A-lines, in the present embodiment called A-line image/frame which forms the 2D OCT frame when translated to Cartesian coordinates, may be selected (see e.g., step S102) and prepared for processing. During the process preparation or frame preprocessing (see e.g., step S104), pixels which correspond to the catheter or probe and artifact and/or extravascular tissue areas may be set to zero (see e.g., FIG. 6) and mean filtering (7×7) may be applied. FIG. 6 shows at least one embodiment example of a scan mode setting of an OCT system or systems of the present disclosure and at least one embodiment of the preprocessing of the current frame. For example, the A-line image (upper right image of FIG. 6) may be smoothed, and the catheter/probe and artifact areas may be removed.

Mean Filtering:

Mean filter may be applied as a spatial filter. In one or more embodiments, a Mean filter may be a sliding window (kernel) spatial filter, which replaces the central value of the window with the mean intensity value of the pixels that belong to the window. For an image I and a window having size N×N, the value of the window's central pixel (i,j) is replaced by the $$M_N: \frac{1}{N \times N} \Sigma_{m,n \in N \times N} I(m, n),$$

where m,n are the pixels belonging to the window N×N, where m, n are the pixels belonging to the window N×N.

In the next step (S106) of the method the filtered image is processed as follows: i) apply Otsu's automatic thresholding, ii) smooth the segmented images by deleting small objects which correspond to image artifacts, and iii) separate the image in four equal parts which correspond to four Cartesian quadrants. This step, from the image thresholding to the A-line and OCT image quadrant correspondence is presented in detail in FIG. 5. While this step is visualized with four equal parts, the present disclosure provides for division into 2, 3, 5, 6, 7, or 8 equal parts. Further, while the parts must be substantially equal in area, the equal parts may have some small variance in the exact number of pixels or A lines in various parts.

In one or more embodiments, other types of filtering may be used, such as, but not limited to, Gaussian filtering, bilateral filtering, etc. For example, similarly to Gaussian filters, bilateral filters are non-linear smoothing filters. The fundamental difference is that bilateral filters take into account the pixels intensity differences, which result in achieving edge maintenance simultaneously with noise reduction. Using convolutions, a weighted average of the neighborhood pixels' intensities may replace the intensity of the mask's central pixel. In one or more embodiments, the bilateral filter for an image I, and a window mask W is defined as:

$$I'(x) = \frac{1}{W_p} \Sigma_{x_i \in w} I(x_i) f_r(\|I(x_i) - I(x)\|) g_s(\|x_i - x\|),$$

having a normalization factor $W_p$: $W_p = \Sigma_{x_i \in w} f_r(\|I(x_i) - I(x)\|) g_s(\|x_i - x\|)$, where x are the coordinates of the mask's central pixel and the parameters $f_r$ and $g_s$ are the Gaussian kernel for smoothing differences in intensities and the spatial Gaussian kernel for smoothing differences in coordinates.

Figure 7:
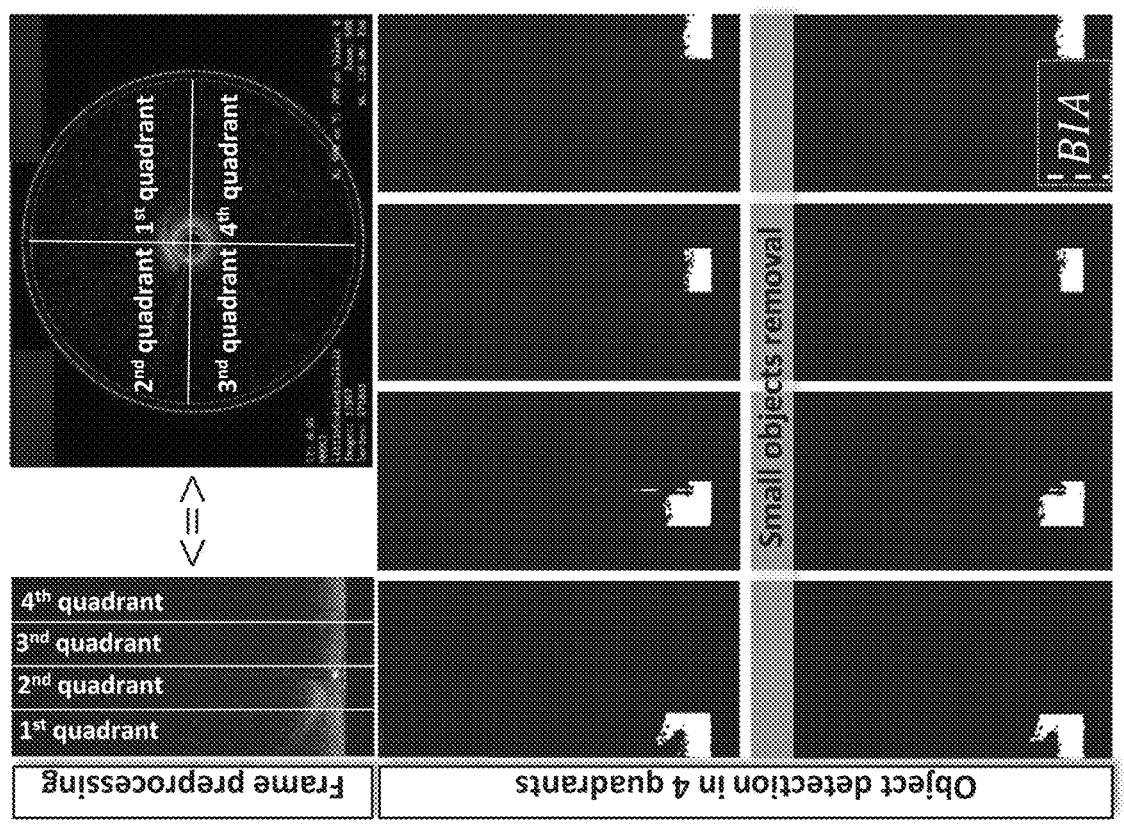
FIG. 7 is at least one embodiment example of an object detection and the A-line and OCT images quadrant correspondence in accordance with one or more aspects of the present disclosure.

In one or more embodiments of step S106 (see e.g., FIG. 5, etc.), the filtered image may be processed, and image segmentation may be applied, as follows: (i) applying automatic thresholding, such as, but not limited to, Otsu's automatic thresholding; (ii) smoothing the segmented images by deleting small objects which correspond to image artifacts; and (iii) separating the image into four equal parts, which correspond to four Cartesian quadrants. At least one embodiment of step S106, from the image thresholding to the A-line and OCT image quadrant correspondence is presented in detail in FIG. 7. FIG. 7 shows at least one embodiment example of the object detection and the A-line and OCT images quadrant correspondence. The objects may be compared to the $T_{dis}$ value to decide whether the objects belong to blood or not.

Figure 8:
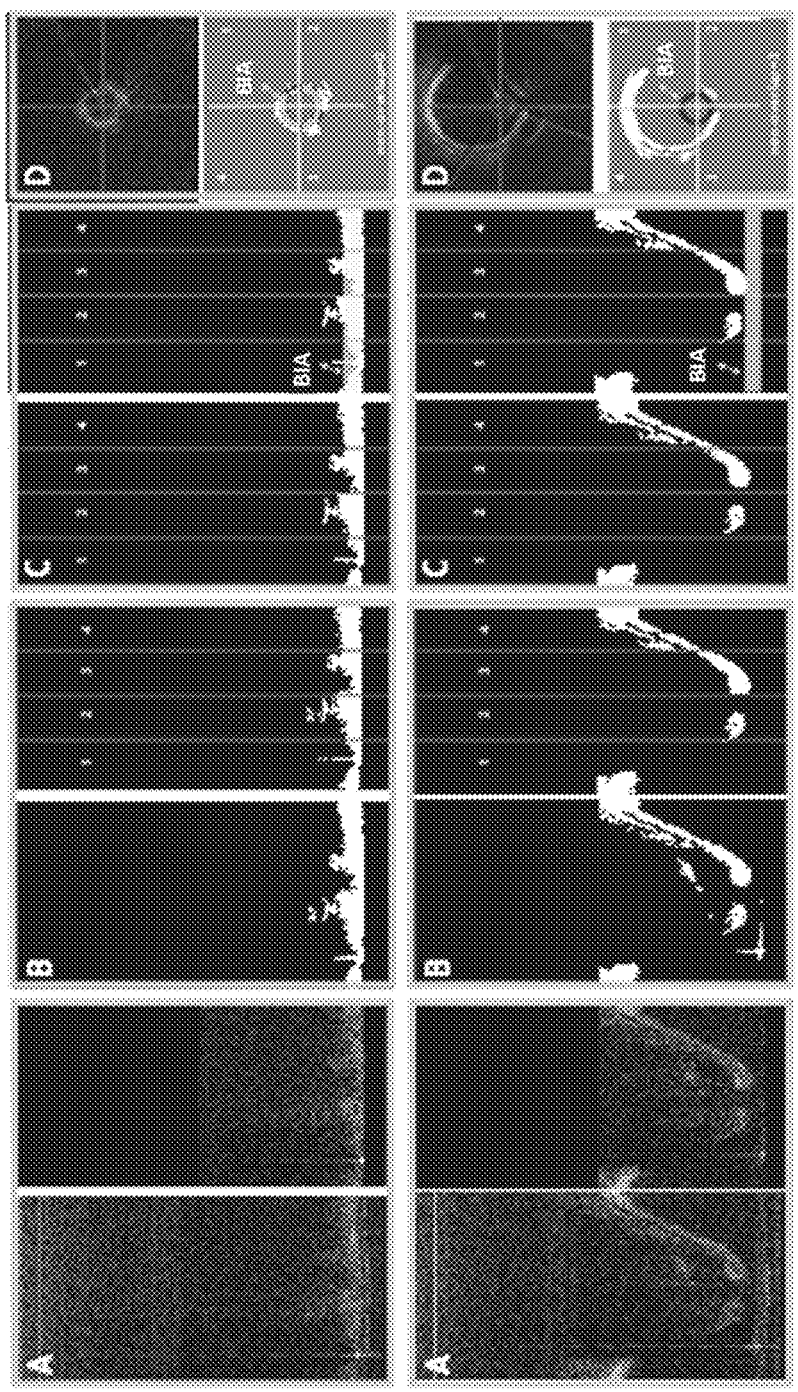
FIG. 8 shows a schematic description of at least one embodiment of an auto-pullback method for an image having blood (top panel) and a flushed image (bottom panel) in accordance with one or more aspects of the present disclosure.

FIG. 8 (which includes portions A through D of the top and bottom panels of FIG. 8) shows a schematic description of at least one embodiment of an auto-pullback method for an image having blood (top panel) and a flushed image (bottom panel). Portion A of FIG. 8 shows an A-line image cleaned from the catheter or probe (e.g., the catheter or probe 120) and extravascular background. Portion B of FIG. 8 shows an image thresholded, equally divided, and with small objects removed. Portion C of FIG. 8 shows binary objects and the BIA area. Portion D shows non-overlapping objects counted in the corresponding Cartesian image.

Figure 9:
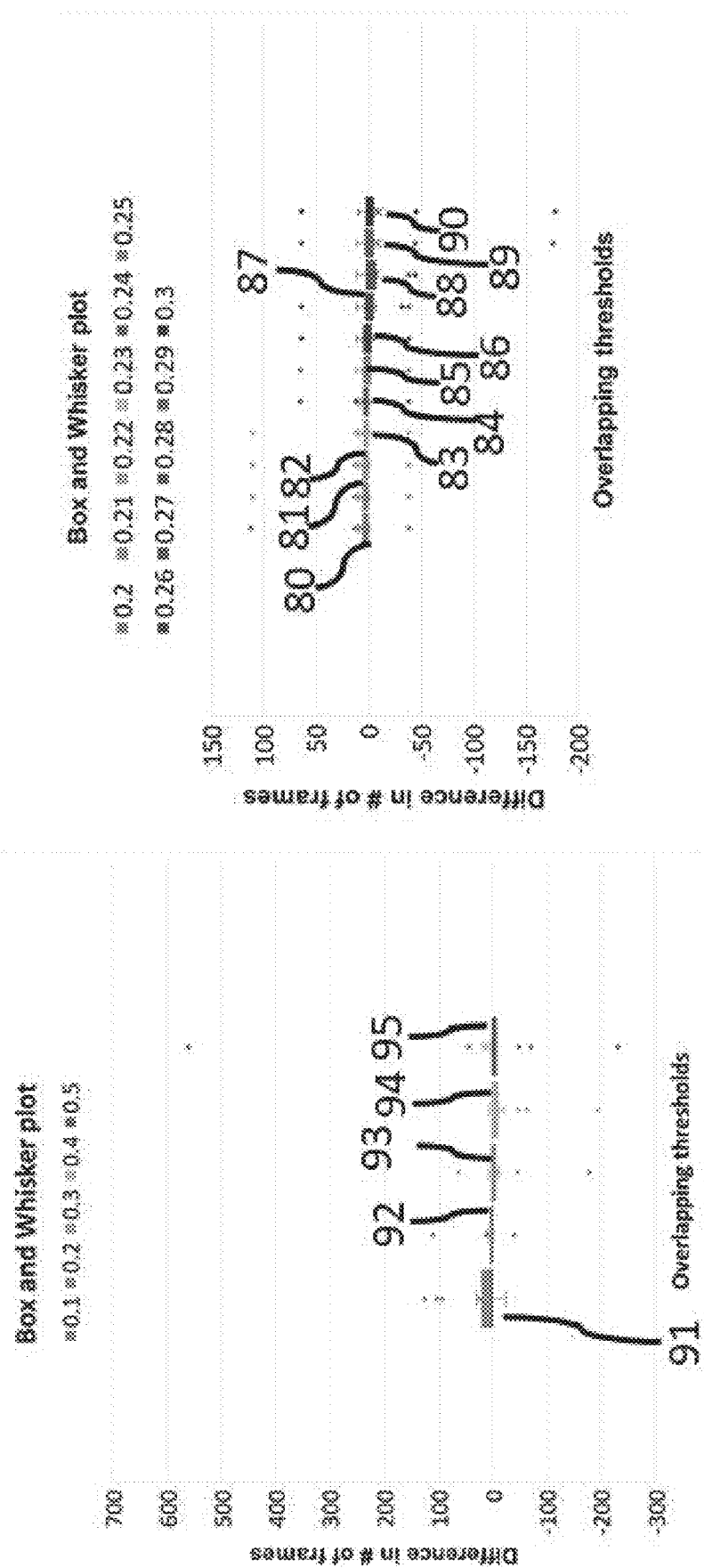
FIG. 9 shows a sensitivity analysis that was conducted for object deleting percentage threshold(s) in accordance with one or more aspects of the present disclosure.

Otsu's Thresholding:

In one or more embodiments, to automatically threshold the A-line images, for example, a threshold $Thr_{otsu}$ for an image I may be calculated using the Otsu's method, and the pixels of the image I that are smaller than $Thr_{otsu}$ may set to zero value. The result is a binary image with the arterial wall and blood represented by the non-zero objects. Since the non-zero objects might also correspond to image artifacts, an extra step may be applied in one or more embodiments: detecting the objects that are smaller than a predetermined area, such as, but not limited to, a whole catheter or probe area, 3% of the whole image, etc. Using this extra step, one or more embodiments ensure that only the objects that correspond to the wall area will be used to detect the border. In one or more embodiments, the extra step may include or may alternatively be: detecting the larger object and deleting the objects which are smaller than the larger object by a predetermined percentage (e.g., 24%, 20%, 25%, 30%, any value in the range of about 10% to about 50%, any value in the range of 10% to 50%, any value in the range of about 20% to about 30%, any value in the range of 20% to 30%, etc.). A sensitivity analysis that was performed on the deleting percentage is shown in FIG. 9. The left portion of FIG. 9 illustrates a Box and Whisker plot showing, for one or more embodiments, an ideal or optimal frame difference being achieved when using object deleting thresholds 0.2 (24%) and 0.3 (30%) within the range of 0.1-0.5 (10-50%) (The overlapping thresholds of 0.1 (91), 0.2 (92), 0.3 (93), 0.4 (94), and 0.5 (95) are shown from left to right, respectively, on the left portion of FIG. 9). The right portion of FIG. 9 illustrates a Box and Whisker plot showing an ideal or optimal frame difference being achieved when using object deleting threshold 0.24 (24%), within the range of 0.2-0.3 (20-30%) (The overlapping thresholds of 0.2, 0.21, 0.22, 0.23, 0.24, 0.25, 0.26, 0.27, 0.28, 0.29, and 0.3 are shown from left to right, respectively, on the right portion of FIG. 9).

Figure 10:
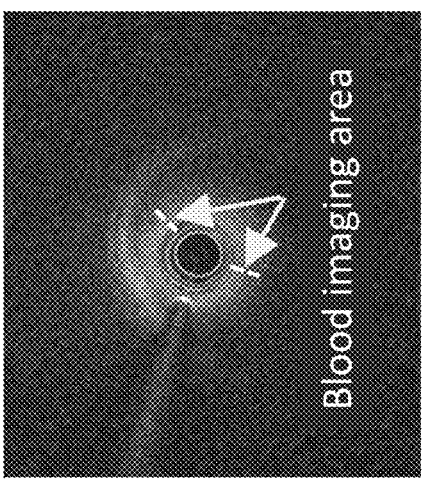
FIG. 10 shows at least one embodiment of OCT imaging of blood (left side of FIG. 10) and a circular area, which includes the majority of the image or imaged blood (right side of FIG. 10), in accordance with one or more aspects of the present disclosure.
Figure 11:
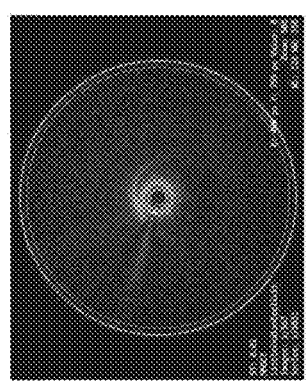
FIG. 11 shows at least one embodiment example of a length of blood imaging ($=T_{dis}$) before the blood flushing occurs (e.g., OCT allows a specific or predetermined imaging depth when blood is present—also referred to herein as blood imaging area (BIA)) in accordance with one or more aspects of the present disclosure.

In one or more embodiments of step S108, binary objects relative position(s) may be considered. For example, in one or more embodiments, a relative position of each detected binary object to the blood imaging area (BIA) may be calculated. As BIA, a circular area above the catheter or probe tip may be denoted. This concept derives from the fact that before flushing occurs and the lumen borders are revealed, blood encircles the catheter or probe (e.g., the catheter or probe 120) at a specific distance. An example of the BIA area in a pre-flushed image is shown in FIG. 10, which shows OCT image of blood (left side of FIG. 10) and the circular area which includes the majority of the image or imaged blood (right side of FIG. 10). Using BIA as a reference area, the overlapping and non-overlapping binary objects to the BIA may be calculated (see e.g., portion C of FIG. 8).

Additionally or alternatively, in one or more embodiments of step S108, the relative position of each object may be calculated as: counting how many binary objects are above a specific distance, $T_{dis}$, from the catheter or probe (e.g., the catheter or probe 120). Denoting catheter or probe distance, the number of pixels that are above a specific height form the catheter or probe tip in one or more embodiments. The concept of inserting the catheter or probe distance derives from the fact that before flushing clears the blood and reveals the lumen borders, blood encircles the catheter or probe (e.g., the catheter or probe 120) at a specific distance since OCT allows a specific imaging depth when blood is present (see example image shown in FIG. 11; the length of blood imaging area (BIA) before the blood flushing occurs. OCT allows a specific imaging depth when blood is present). To define the BIA, the length depth was measured at different blood state images, and the measurements were averaged. One or more of the algorithm or method embodiments aim at detecting how many objects were moved over the OCT's blood imaging.

Depending on the relative position of each binary object the algorithm or method embodiment(s) next decides/decide about the clearing condition (see e.g., step S110) of the processed frame. If the number of objects not overlapping the BIA are a predetermined threshold (e.g., 3) or more (in one or more embodiments, the threshold may be set at at least one or more of the following: 2 or more, 3 or more, 4 or more, 5 or more, a predetermined number or more, etc.), this means that in the current frame the vessel wall is becoming visible. However, wall visibility may change from frame to frame (e.g., where a wall is visible in one frame, the wall may not be visible in the next frame). This is due to the heart and vessel movement during systole and diastole and due to the flushing pressure variability, which is controlled by the user. Therefore, in one or more embodiments, a counter is incorporated and set to zero from the beginning of the algorithm(s) or method(s). In the case of wall visibility in the current frame, one is added to the counter (see e.g., step S112), otherwise the counter is set to zero again (see e.g., S116). For example, at least one embodiment having an object overlapping with the BIA or not overlapping the BIA is shown in FIG. 12.

When one is added to the counter (S112), then the next step is to check if, for a predetermined number (e.g., three, four, five, six, etc.) frames in a row (e.g., when the counter equals 5 or the predetermined number set), the arterial wall was visible (see e.g., step S114). If "no", the algorithm moves to the next frame; otherwise, if "yes", the pullback is triggered (see e.g., step S114). Having the counter ensures that the blood is cleared enough so the pullback may be synchronized with an improved or optimal clearing state.

Figure 12:
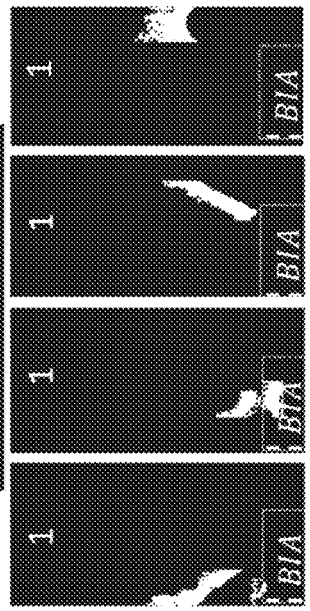
FIG. 12 shows at least one respective embodiment example of two application examples, one being of a non-flushed frame (left side of FIG. 12) and one of a flushed frame (right side of FIG. 12)(e.g., in one or more embodiments, the detected moving objects on the flushed image may be four (4) while on the non-flushed zero (0)) in accordance with one or more aspects of the present disclosure.

Two application examples: one of a non-flushed frame and one of a flushed frame are shown in FIG. 12; the detected objects in the non-flushed is zero (see left side of FIG. 12) while, in the flushed frame, the detected objects are four (see right side of FIG. 12). In one or more embodiments, depending on the relative position of each binary object, the method(s) decide(s) about the clearing condition of the processed frame. If the number of non-overlapping to BIA objects is greater than three (or another set or predetermined threshold), this may indicate that the arterial wall is revealed or visible and that the blood is flushed (e.g., indicates a clearance state). However, since blood clearance may be present in one frame and not in the next frame and to minimize the clearance state detection error, a counter may be added. The counter, which is initially set to zero, may be increased by one each time a clearance state is detected, and the pullback may start when the counter reaches a predetermined number (e.g., 3, 4, 5, etc.) (see e.g., FIG. 3, FIG. 8D, etc.).

One or more embodiments may provide one or more of the following advantages or benefits: (i) By dividing an image to four parts/quadrants and studying the flushing state in each part, the method ensures that the flushing state may be detected even in small diameter vessels (for example, when the diameter of the vessel is small, there is a difficulty in discriminating between blood, lumen, and catheter or probe objects (the catheter or probe often may be touching a wall of a lumen or vessel); (ii) By applying a counter in at least one method embodiment, optimal pullback flushing synchronization may be achieved (for example, sequential frames may be detected as clear before the pullback starts avoiding imaging loss); and/or (iii) By applying one or more features of the present disclosure, no user interaction is needed, or may be optional, since automatic thresholding is performed.

While the present disclosure is not limited to the below features, one or more features of the present disclosure are summarized below:

triggering; and preventing the use of or avoiding a second flushing such that risk to a patient is reduced or minimized.

One or more of the methods of the present disclosure was used to apply the automatic pullback method(s) using in vivo animal data. One or more of the automatic pullback method(s) may be used with one or more imaging modalities, such as, but not limited to, MM-OCT, NIRAF, IV-OCT, etc. In one or more embodiments, an MM-OCT catheter or probe that was used included a dual mode, fiber optic, intravascular imaging catheter or probe. MATLAB was used to perform calculations and/or process one or more features of the automatic pullback method(s).

While the present invention has been described with reference to exemplary embodiments, it is to be understood that the invention is not limited to the disclosed exemplary embodiments. The scope of the claims is to be accorded the broadest interpretation so as to encompass all modifications, equivalent structures, and functions.

Additional Details and Auto-Pullback Experiments Conducted:

At least one purpose of these experiments/report portion is to present at least one automatic pullback algorithm, test the at least one algorithm using retrospective experimental data and interpret the results. The algorithm reduces the experts' tasks during the OCT imaging procedure, reduces the possibility of an unsynchronized flushing-pullback to occur, and ensures that the whole targeted vessel will be imaged. The scope includes the application of the automatic pullback algorithm using in vivo animal data.

Definitions

| Term/Acronym | Definition |
|---|---|
| MMOCT | Multi-Modality Optical Coherence Tomography |
| NIRAF | Near-infrared autofluorescence |

| Key features of invention | Improvement |
|---|---|
| Detect the cleared lumen state in four part/quadrants | The flushing state can be detected even in small diameter vessels. Detecting the moving binary objects of the four quadrants in small diameter vessels is more robust than comparing radiuses/rings which will be very close due to the small artery diameter. |
| Incorporating a counter (S112 & S116) | Measuring how many frames in a row have a blood clear state ensures that optimal pullback-flushing synchronization. |
| No user interaction | One or more embodiments of a method of the present disclosure do not require any parameters to be modified by the user to adjust the behavior of the flush clearing state, when the algorithm fails. One or more methods of the present disclosure do not need any user interaction. |

As aforementioned, one or more method embodiments of the present disclosure reduce tasks (e.g., for an expert, a medical practitioner, a clinician, etc.) during an OCT imaging procedure, reduces the possibility of an unsynchronized flushing-pullback to occur, and ensures that a whole targeted vessel (or other predetermined target) is or will be imaged.

One or more embodiments of the present disclosure may involve a method for triggering an automatic pullback during imaging (e.g., intravascular imaging), and may include the following: synchronizing the flushing and catheter or probe pullback states in imaging (e.g., OCT imaging); reducing or minimizing the medical experts tasks during intravascular imaging; reducing or minimizing the pullback imaging loss caused by late or early pullback -continued

| Term/Acronym | Definition |
|---|---|
| BIA | Blood imaging area |
| A-line | Optical Coherence Tomography image in polar coordinates |
| image | |

Dataset

At least one embodiment of the algorithm and/or method was tested on retrospective image data using two different ex vivo datasets produced during EP 1-3 (HORL-ENG-00250) and EP 2-1 (HORL-ENG-00665) systems animal (swine)

testing. The data were acquired under a specific protocol which is described in HORL-RPT-00038 and HORL-RPT-00070 for the study which used EP 1-3 and EP 2-1 systems, respectively. 17 pullbacks were acquired including the pre-flushing frames and were used for developing and testing the current algorithm and/or method embodiment. Blood clearance was performed using contrast in the majority of the pullbacks (saline was used in one pullback), the injection was either manual or automatic, and two different catheters or probes were used in each system. A summary of the MMOCT pullbacks used in the experiments is presented in detail in FIG. 13.

Results

Gold Standard or Ground Truth

Two experts, one of whom is the inventor, 1 and 2 examined independently the current dataset and detected the clearance frame in each pullback. Clearance frame was defined as the frame that shows at least the three quarters (270°) of the vessel's wall structure. To define the inter-observer variability acceptance limit, the time delay between experts during the manual pullback was accounted. During the manual pullback procedure, there might be a disagreement/delay between experts on pressing the pullback button which is acceptable around 0.5 sec. The pullback is 400 frames and it lasts 2 seconds; therefore, the 0.5 sec is equal to 100 frames and was used as the variability acceptance limit. The difference between results (difference in number of frames against the number of pullbacks) obtained by expert 1 and expert 2 is shown in FIG. 14A (the inter-observer difference).

Algorithm Assessment Metrics

To assess the auto-pullback algorithm or method embodiment in the experiment, quantitative and qualitative measurements were used. The quantitative measurements include the difference in frames between the algorithm or method and the experts: frame clearance detected by the algorithm minus frame clearance (mean) observed by the experts. The results are presented in FIG. 14B (the algorithm's or method's versus the two experts (mean) difference). Since the goal of the auto-pullback algorithm or method embodiment is to start the pullback automatically and all the pullback frames to be in a clearance state, a second qualitative assessment measurement was added: the visual inspection of the longitudinal views (vertical and horizontal). Using the qualitative measurement: (i) a second checkpoint was performed by visually inspecting if all the algorithm's or method's clearance frame detection provides a clear pullback, and (ii) the quality of the pullback was assessed.

Figure 16A:
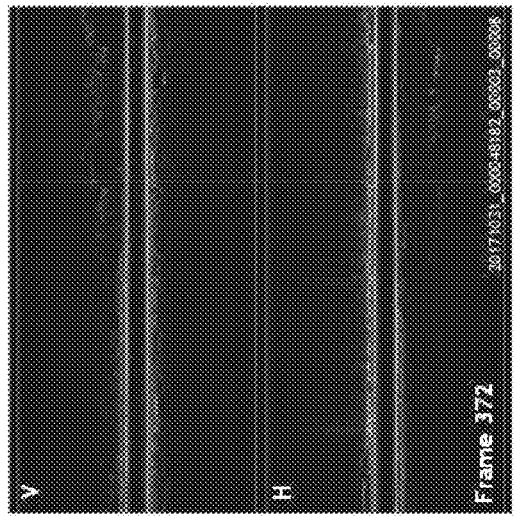
FIGS. 16A-16Q include qualitative results on longitudinal views for seventeen (17) pullbacks performed in experiments using an auto-pullback method or algorithm in accordance with one or more aspects of the present disclosure.
Figure 16B:
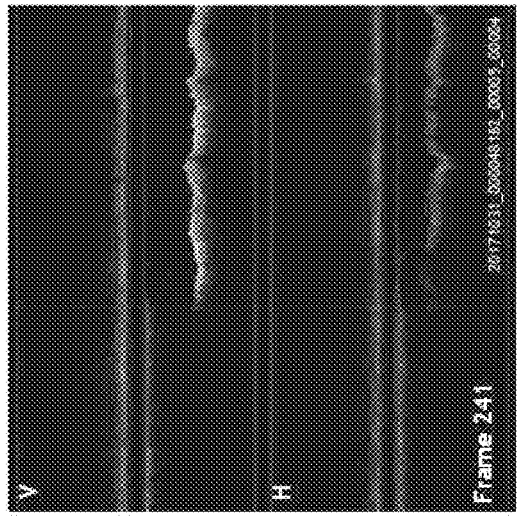
Figure 16C:
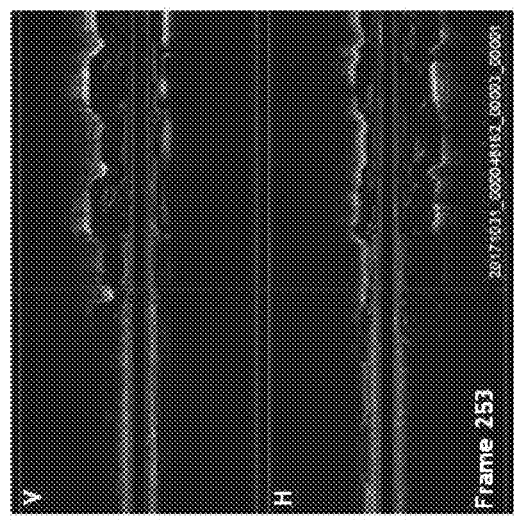
Figure 16D:
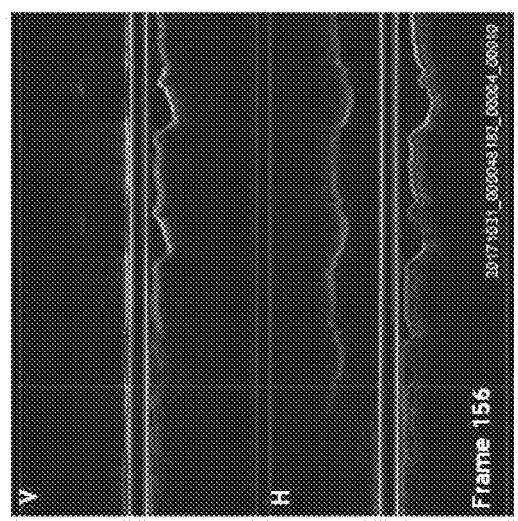
Figure 16J:
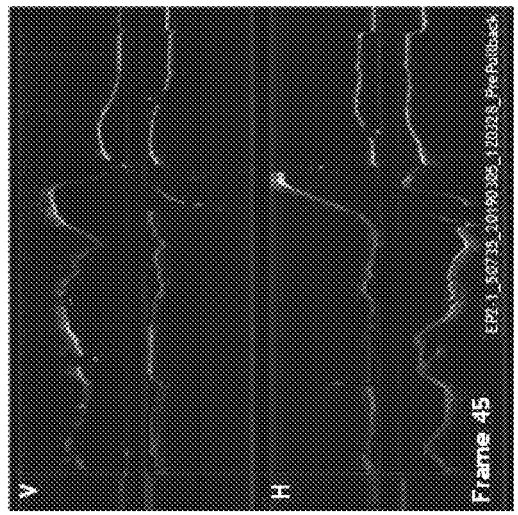
Figure 16L:
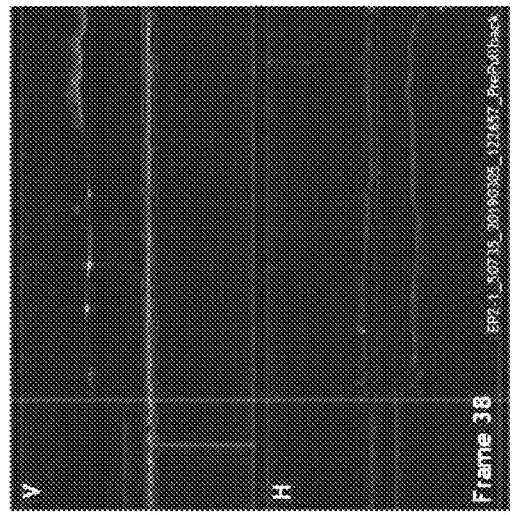
Figure 16I:
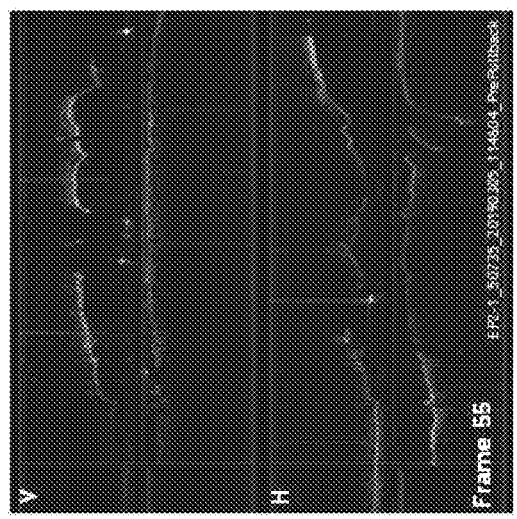
Figure 16K:
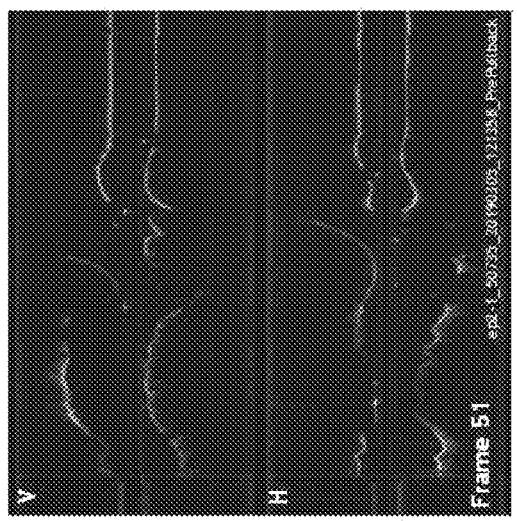
Figure 16M:
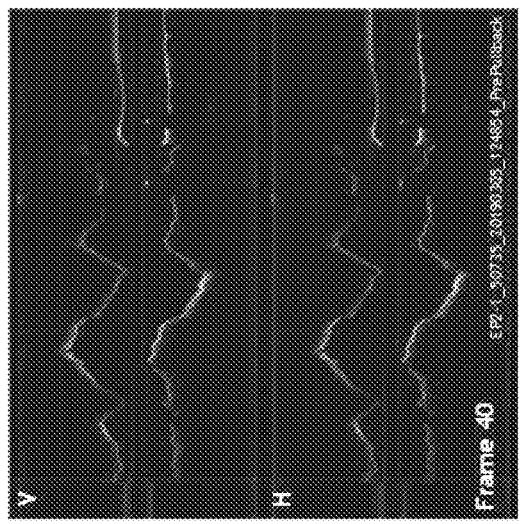
Figure 16N:
Figure 16O:
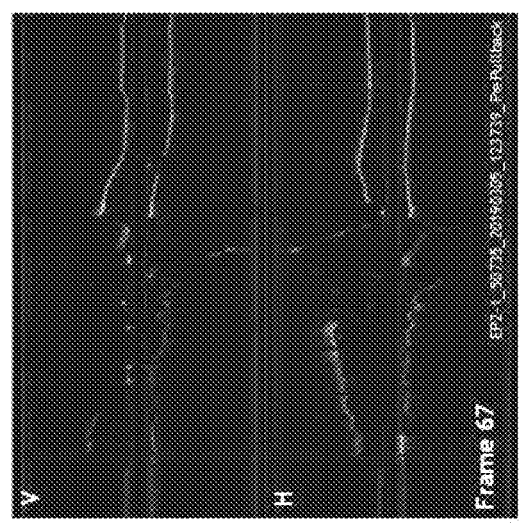
Figure 16P:
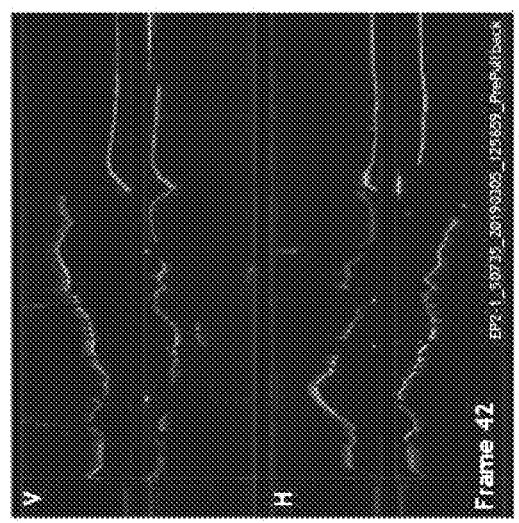
Figure 16Q:
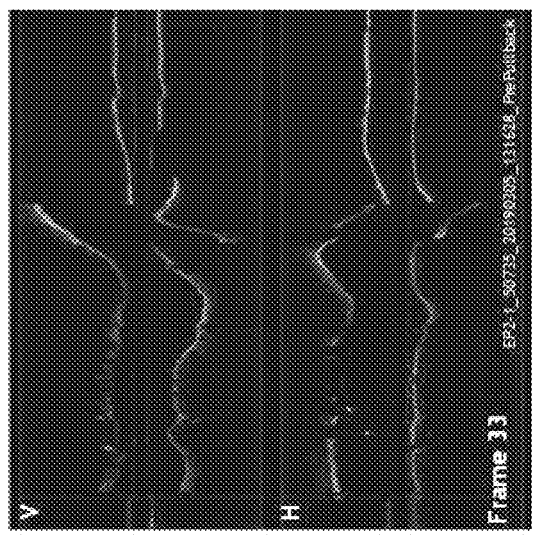

Two examples of the qualitative assessment are shown in FIGS. 15A-15B and the rest are presented in FIGS. 16A-16Q (qualitative results on longitudinal views). By visually inspecting the longitudinal views in two different directions (2D orthogonal cut planes), the quality difference of the two pullbacks may be noticed: pullback A has superior quality compared to pullback B. Pullback A corresponds to pullback #14 (FIG. 13 and FIG. 16N, where FIGS. 16A-16Q show pullback #1 through pullback #17, respectively, which are outlined in FIG. 13) which has an excellent agreement with experts (FIG. 14B) and pullback B corresponds to pullback #2 (FIG. 13 and FIG. 16B) which has a moderate agreement with experts (FIG. 14B). Regardless of the imaging quality, both pullbacks pass the 0.5 sec (100 frames) acceptance limit for one or more embodiments. At least two experiment examples of the qualitative assessment of at least one embodiment of an auto-pullback algorithm or method of the present disclosure was performed in two different pullbacks (Pullback A: #14 shown in FIG. 13 and FIG. 16N and Pullback B: #2 shown in FIG. 13 and FIG. 16B as aforementioned). Two different longitudinal views of the orthogonal cut planes were visually inspected to check (i) if the clearance state existed in the frames that follow after the clearance detection frame (vertical line 1500—see e.g., FIGS. 15A and 15B); and (ii) the flushing quality. As shown in FIG. 15A, the imaging quality is great, and the algorithm or method embodiment successfully detected the clearance frame with excellent agreement (algorithm frame 40 vs experts frame 43). As shown in FIG. 15B, the imaging quality is not suitable for guiding an intervention, and the algorithm or method embodiment successfully detected the clearance frame with moderate agreement (algorithm frame 372 vs experts frame 334).

Time Complexity

Figure 17:
FIG. 17 is a graph illustrating time complexity of at least one auto-pullback method or algorithm embodiment in processing 2500 frames in accordance with one or more aspects of the present disclosure.

To access the time complexity of the algorithm or method used in the experiments, a timer was set in the beginning and end of the algorithm or method. FIG. 17 presents the time complexity of the auto-pullback algorithm or method embodiment when applied to 2500 frames. The average time to process a single frame was 0.029 sec. The method(s) was/were implemented in Matlab and ran in a laptop with the following characteristics: AMD Ryzen PRO 2500U w/Radeon Vega Mobile Gfx 2.00 GHz processor, 8.00 GB RAM memory and on 64-bit Windows 10 operating system.

Discussion of the Experiments

At least the auto-pullback method or algorithm used in the experiments aimed to: process each frame during the full speed rotation of the MMOCT system, detect the clearance state (blood free vessel) of the vessel during the contrast injection process, and automatically trigger the pullback.

Overall Performance

The at least one algorithm or method was assessed on pre-recorded imaging data, and experts' estimations on the first clearance frame were used as the aforementioned "gold standard" or basis of comparison. Although the experimental dataset (17 pullbacks) may be viewed as being a small number performed, the results suggest that the method or algorithm embodiment used for the experiments may be robust in various quality pullbacks. A good quality pullback is considered a pullback in which the clearance state starts at once and allows for clear imaging for the whole pullback (e.g., pullback #3 discussed or shown in FIG. 13 and FIG. 16C). A low quality pullback is considered a pullback in which the clearance state is taking time to occur, the vessel wall is not fully revealed, and the clearance state does not last long (e.g., pullback #2 discussed or shown in FIG. 13 and FIG. 16B). The algorithm or method used for the experiments managed to detect the first clearance state frame in all 17 pullbacks, and was in excellent agreement with the experts' estimations in 15 of the pullbacks and in moderate agreement in 2 of the pullbacks (pullbacks #1, 2 discussed or shown in FIG. 13 and FIGS. 16A-16B). It should be noted that the moderate agreement was in pullbacks either having low quality (pullback #2 discussed or shown in FIG. 13 and FIG. 16B) or having a lot of noise (residual blood: pullback #1 as discussed or shown in FIG. 13 and FIG. 16A).

Real-Time Application

Since one or more embodiments of the algorithm(s) or method(s) may be applied in real-time, time performance is of high importance. The experiment results reported that the algorithm or method used for the experiments used an average of 0.029 sec to process an image. Since the MMOCT system or device in full speed acquires 400 frames per 2 sec, any algorithm or method embodiment of the present disclosure designed for real-time application may use an average processing speed of 0.005 sec. The experimental implementation of the algorithm or method embodiment implemented in Matlab may practically process every $6^{th}$ frame. However, the final implementation may be in C++, which may be at least ten times faster than Matlab, and should be able to cover or achieve the real-time metric of 0.005 sec per frame that may be used in one or more embodiments.

The OCT (e.g., IV-OCT, MM-OCT, etc.) system may be any system or apparatus discussed herein, including, but not limited to, system 100, system 100', system 100", system 100''', etc. Indeed, one or more of the subject devices or systems may operate to perform one or more embodiments of an auto-pullback method or algorithm in accordance with one or more features of the present disclosure.

A computer, such as the console or computer 1200, 1200', may perform any of the steps, processes, and/or techniques discussed herein for any apparatus and/or system being manufactured or used, including, but not limited to, apparatus or system 100, apparatus or system 100', apparatus or system 100", apparatus or system 100''', any of the embodiments shown in FIGS. 1-23, any other apparatus or system discussed herein, etc.

Figure 18:
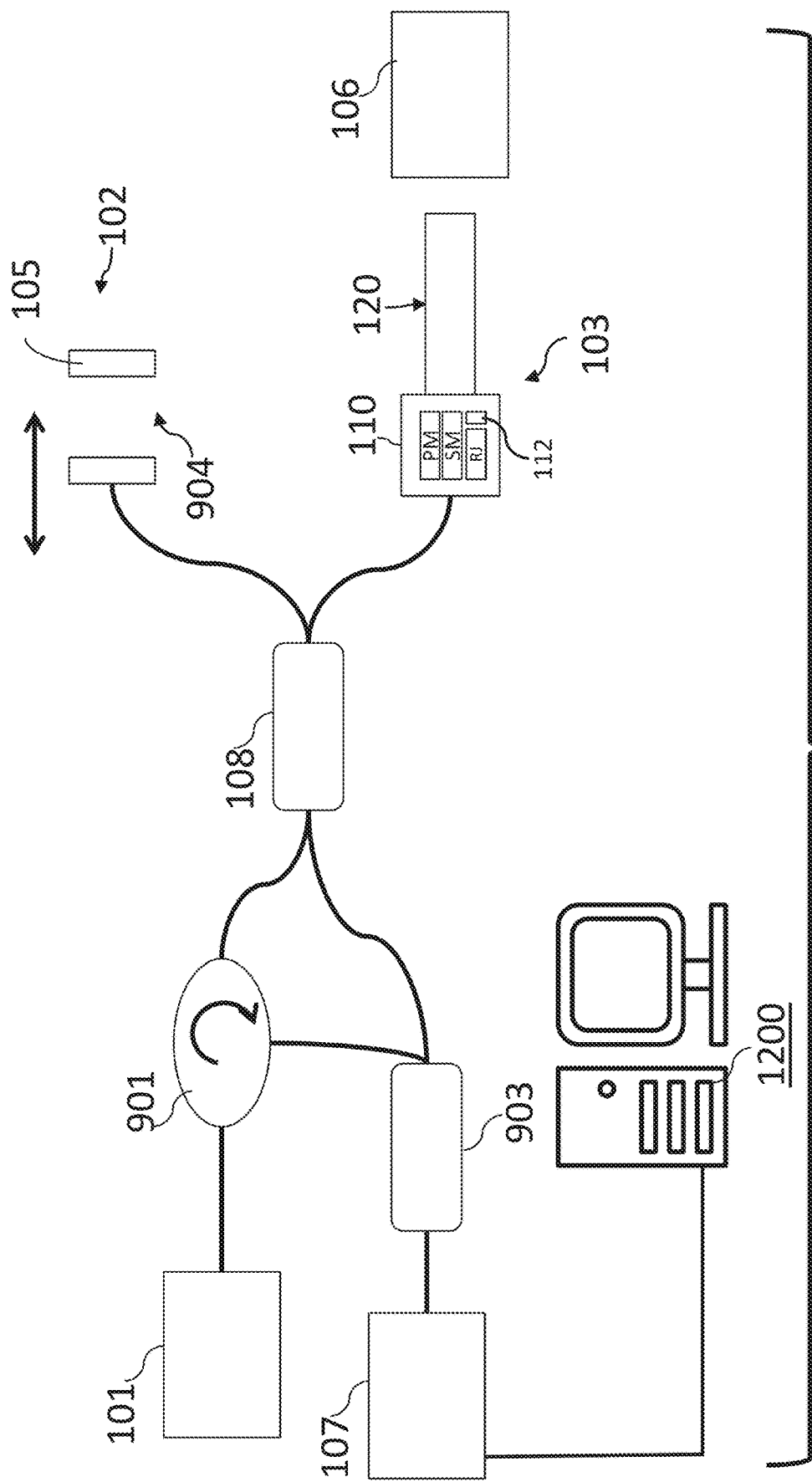
FIG. 18 shows at least one embodiment of an OCT apparatus or system for utilizing one or more embodiments of auto-pullback triggering methods and/or techniques in accordance with one or more aspects of the present disclosure.

In accordance with one or more further aspects of the present disclosure, bench top systems may be utilized with the techniques, such as, but not limited to, the auto-pullback techniques, disclosed herein. FIG. 18 shows an example of a system that can utilize the lumen distance calculation techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target, patient (e.g., a blood vessel of a patient), an object 106, etc. in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 18-20 and 22 discussed further below), the computer 1200' (see e.g., FIG. 23 discussed further below), etc. Additionally or alternatively, one or more of the computers, CPUs, processors, etc. discussed herein may be used to process, control, update, emphasize, and/or change one or more of the multiple imaging modalities, and/or process the related techniques, functions or methods (e.g., the auto-pullback method(s) or algorithm(s)), or may process the electrical signals as discussed above.

Figure 19:
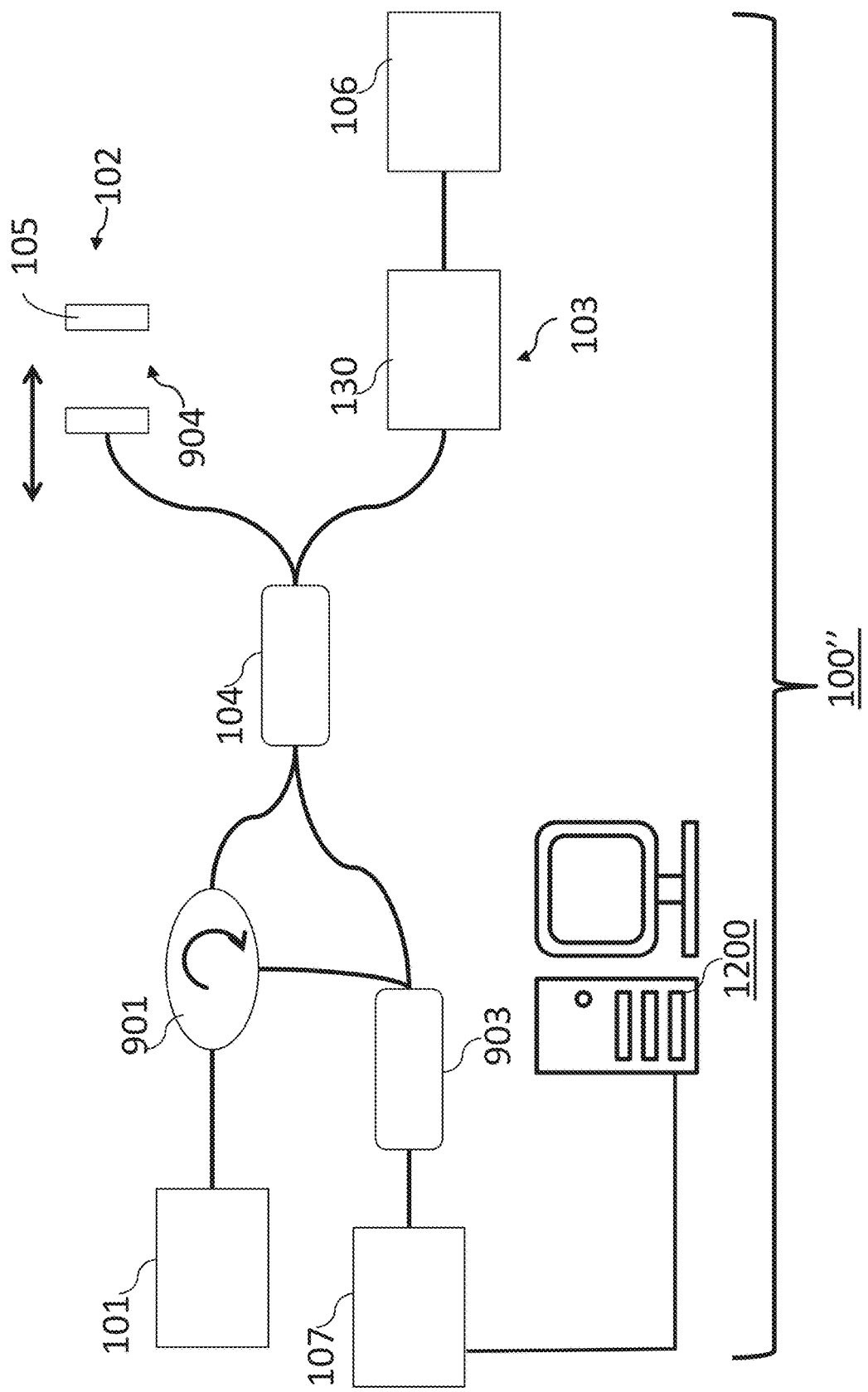
FIG. 19 shows at least another embodiment of an OCT apparatus or system for utilizing one or more embodiments of auto-pullback triggering methods and/or techniques in accordance with one or more aspects of the present disclosure.

In one or more embodiments, the sample arm 103 may include a phase shift unit 130 for a bench top system(s) as shown in system 100" in FIG. 19. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 18-20) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, lumen distance, or any other measurement discussed herein, to perform auto-pullback method(s) or algorithm(s), and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 20:
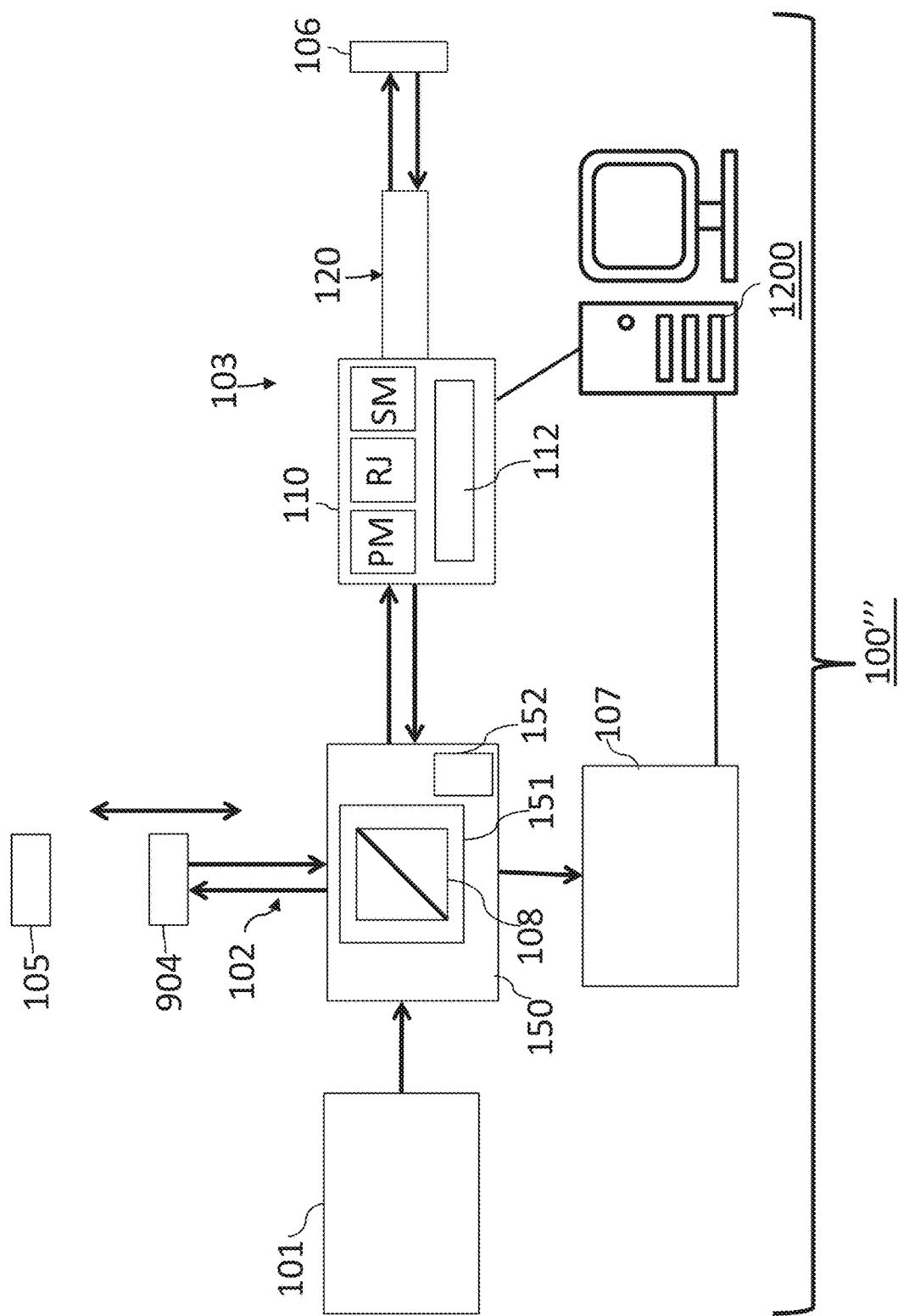
FIG. 20 shows at least a further embodiment of an OCT apparatus or system for utilizing one or more embodiments of auto-pullback triggering methods and/or techniques in accordance with one or more aspects of the present disclosure.

In accordance with one or more further aspects of the present disclosure, one or more other systems may be utilized with the lumen distance calculation techniques disclosed herein. FIG. 20 shows an example of a system 100''' that may utilize the auto-pullback techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 18-20 and 22 discussed further below), the computer 1200' (see e.g., FIG. 23 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIGS. 18 and 20). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Preferably, in one or more embodiments including the deflecting or deflected section 108 (best seen in FIGS. 18-20), the deflected section 108 operates to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", 100''', any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the aforementioned configurations of at least FIGS. 1-23 may be incorporated into one or more of the systems, including, but not limited to, the system 100, 100', 100", 100''', discussed herein.

While not limited to such arrangements, configurations, devices or systems, one or more embodiments of the devices, apparatuses, systems, methods, storage mediums, GUI's, etc. discussed herein may be used with an apparatus or system as aforementioned, such as, but not limited to, for example, the system 100, the system 100', the system 100", the system 100''', the devices, apparatuses, or systems of FIGS. 1-23, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the multiple imaging modalities, to calculate lumen distance(s), to perform auto-pullback method(s) or algorithm(s), and/or process the related techniques, functions or methods, or may process the electrical signals as discussed above.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing control, viewing, changing, emphasizing methods for one or more imaging modalities and/or any other method discussed herein. The light source 101 may be fiber coupled or may be free space coupled to the other components of the apparatus and/or system 100, 100', 100", 100''', the devices, apparatuses or systems of FIGS. 1-23, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 1-23 and as discussed above.

The one or more detectors 107 may transmit the digital or analog signals to a processor or a computer such as, but not limited to, an image processor, a processor or computer 1200, 1200' (see e.g., FIGS. 1, 18-20, and 22-23), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-23, the computer 1200, the computer 1200', the image processor, may also include one or more components further discussed herein below (see e.g., FIGS. 22-23).

In at least one embodiment, a console or computer 1200, 1200' operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 18-20 and FIG. 22 and/or the console 1200' of FIG. 23 as further discussed below). In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", 100''', and/or the detector(s) 107 thereof, and/or from the devices, apparatuses, or systems of FIGS. 1-23, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems/apparatuses, such as, but not limited to, the system 100, the system 100', the system 100", the system 100''', the systems/apparatuses of FIGS. 1-23, etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100''', etc. as discussed herein. Those skilled in the art will appreciate that alternative embodiments of the system 100, the system 100', the system 100", the system 100''', the systems/apparatuses of FIGS. 1-23, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', the systems/apparatuses of FIGS. 1-23, any other embodiment, etc. as discussed herein, there are similarities between the apparatuses/systems discussed herein. Likewise, while the console or computer 1200 may be used in one or more systems (e.g., the system 100, the system 100', the system 100", the system 100''', the systems/apparatuses of FIGS. 1-23, etc.), one or more other consoles or computers, such as the console or computer 1200', may be used additionally or alternatively.

Figure 21:
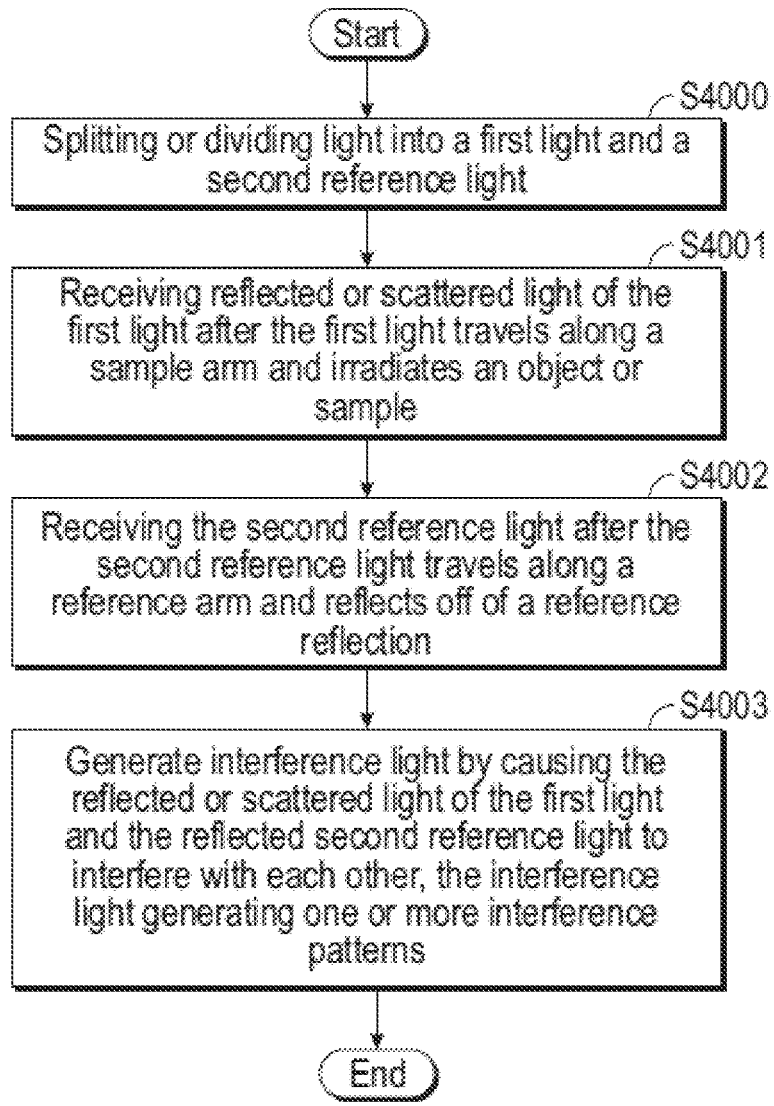
FIG. 21 is a flow diagram showing a method of performing an imaging feature, function or technique in accordance with one or more aspects of the present disclosure.

In accordance with one or more aspects of the present disclosure, one or more methods for detecting and guiding optical connections are provided herein, and one or more methods for performing imaging are provided herein. FIG. 21 illustrates a flow chart of at least one embodiment of a method for performing imaging. Preferably, the method(s) may include one or more of the following: (i) splitting or dividing light into a first light and a second reference light (see step S4000 in FIG. 21); (ii) receiving reflected or scattered light of the first light after the first light travels along a sample arm and irradiates an object or a sample (see step S4001in FIG. 21); (iii) receiving the second reference light after the second reference light travels along a reference arm and reflects off of a reference reflection (see step S4002 in FIG. 21); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 21). One or more methods may further include using low frequency monitors to update or control high frequency content to improve image quality. For example, one or more embodiments may use balanced detection, polarization diversity, automated polarization control, calculated lumen distance(s), auto-pullback method(s) or algorithm(s), etc. to achieve improved image quality. In one or more embodiments, an imaging probe may be connected to one or more systems (e.g., the system 100, the system 100', the system 100", the system 100''', the devices, apparatuses or systems of FIGS. 1-23, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or detect lumen edge(s) and artifact(s), and/or perform auto-pullback method(s) or algorithm(s), digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1, 18-20, and 22), a computer 1200' (see e.g., FIG. 23), etc. as discussed further below, via cable(s) or wire(s), such as, but not limited to, the cable(s) or wire(s) 113 (see FIG. 22). Additionally or alternatively, the computers or processors discussed herein are interchangeable, and may operate to perform any of the feature(s) and method(s) discussed herein.

Figure 22:
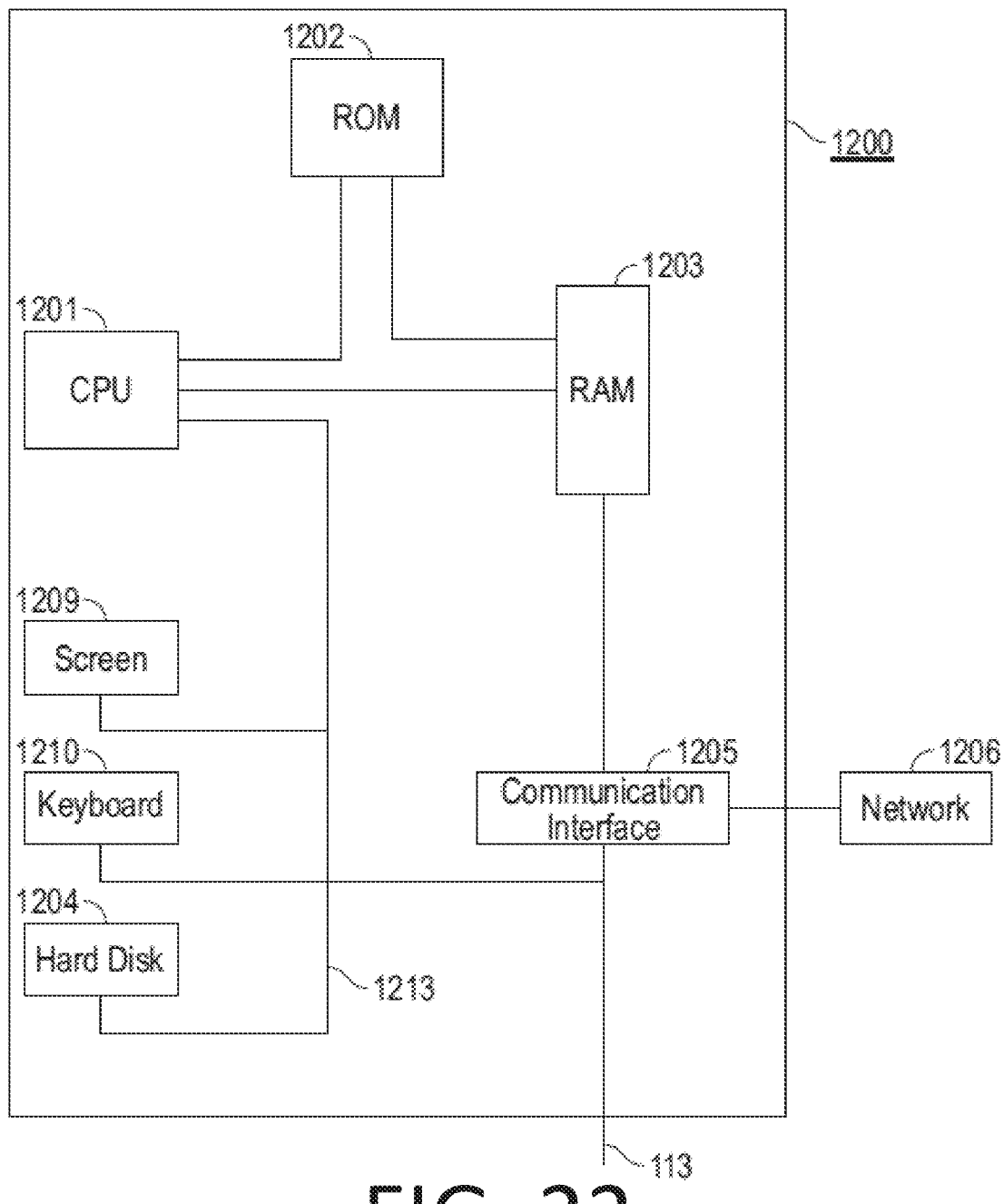
FIG. 22 shows a schematic diagram of an embodiment of a computer that may be used with one or more embodiments of an apparatus or system or one or more methods discussed herein in accordance with one or more aspects of the present disclosure.

Various components of a computer system 1200 (see e.g., the console or computer 1200 as shown in FIGS. 1 and 18-20) are provided in FIG. 22. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., as shown in FIG. 22). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100", the system 100''', and/or the systems/apparatuses of FIGS. 1-23, discussed herein above, via one or more lines 1213), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, and/or lumen distance calculation technique(s), and/or use with auto-pullback technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling, calculation, and/or using technique(s) may be controlled remotely).

Figure 23:
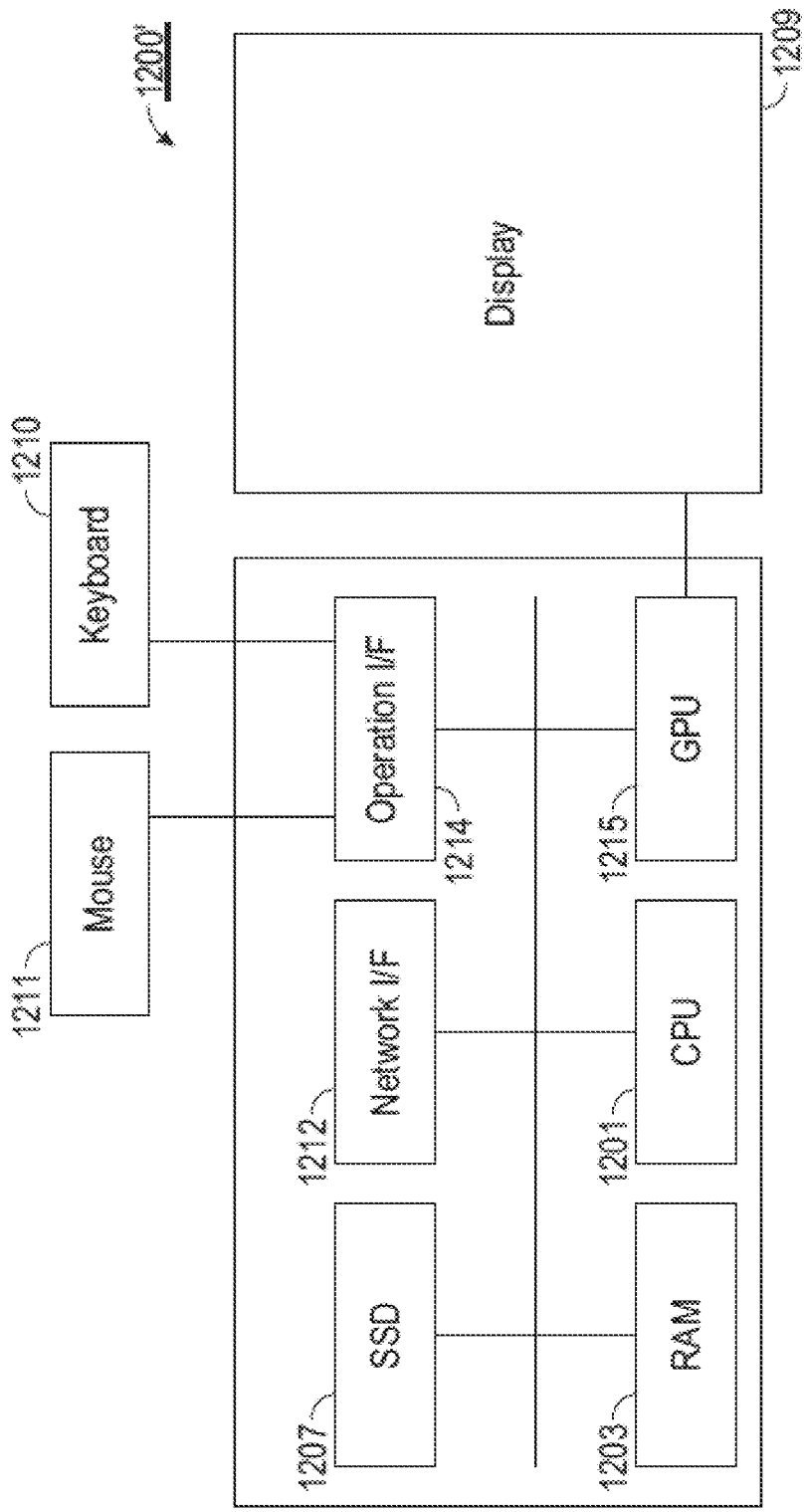
FIG. 23 shows a schematic diagram of another embodiment of a computer that may be used with one or more embodiments of an imaging apparatus or system or methods discussed herein in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 23), a touch screen or screen 1209, a light pen and so on. The communication interface of the computer 1200 may connect to other components discussed herein via line 113 (as diagrammatically shown in FIG. 22). The Monitor interface or screen 1209 provides communication interfaces thereto.

Any methods and/or data of the present disclosure, such as, but not limited to, the methods for using and/or manufacturing a device, system or storage medium for use with same and/or method(s) for imaging, performing tissue or sample characterization or analysis, performing diagnosis, planning and/or examination, detecting lumen edge(s), stent(s), and/or artifact(s), including in OCT image(s), and/or for performing auto-pullback technique(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 23), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 22. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 22 or FIG. 23) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 23. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 18, RJ of FIG. 20, etc.), the motor PM, the motor SM, and/or one or more other components of a system (e.g., the system 100, the system 100', the system 100", the system 100''', the systems/apparatuses of FIGS. 1-23, etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

At least one computer program is stored in the SSD 1207, and the CPU 1201 loads the at least one program onto the RAM 1203, and executes the instructions in the at least one program to perform one or more processes described herein, as well as the basic input, output, calculation, memory writing, and memory reading processes.

The computer, such as the computer 1200, 1200', communicates with the PIU 110, the rotary junction (e.g., the RJ, etc.), the motor PM, the motor SM, the MCU 112, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s), and/or performing auto-pullback technique(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the systems/apparatuses of FIGS. 1-23, etc.) to set or change the imaging condition, and to start or end the imaging, and/or to start or end the lumen detection, stent(s) detection, artifact(s) detection, blood clearance detection and/or performance of auto-pullback technique(s). The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes.

Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, 2016/0228097, 2018/0045501, and 2018/0003481, each of which patents, patent publications and patent application(s) are incorporated by reference herein in their entireties. As aforementioned, any feature or aspect of the present disclosure may be used with the features disclosed in WO 2016/144878, which is incorporated by reference herein in its entirety. As aforementioned, any feature or aspect of the present disclosure may be used with OCT imaging systems, apparatuses, methods, storage mediums or other aspects or features as discussed in U.S. Pat. Pub. 2019/0298174; U.S. patent application Ser. No. 16/131,662; U.S. patent application Ser. No. 16/414,222, filed on May 16, 2019; U.S. Pat. App. No. 62/901,472; U.S. Pat. App. No. 62/925,655; and U.S. Pat. App. No. 62/944,064, filed on Dec. 5, 2019, each of which patent(s), publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures, and functions.

The invention claimed is:

1. An imaging device for triggering an automatic pullback, the device comprising:
an imaging probe; and
one or more processors that operate to:
(a) import a plurality of A-lines, an image, or images;
(b) initialize a counter;
(c) segment the A-lines, the image, or the images;
(d) separate the segmented A-lines, image, or images into three or more equal parts;
(e) define a Blood Imaging Area (BIA), which is an area surrounding the imaging probe in a case where blood is present;
(f) detect a number of objects that are non-overlapping with the BIA, or that are above or over a specific or predetermined distance from the imaging probe, within one frame or a current frame of a plurality of frames of the segmented A-lines, image, or images;
(g) perform a counting step:
in a case where the number of the objects is greater than or equal to N, wherein N is a minimum acceptance number of objects that defines a partial cleared or cleared state, then increase the counter by a set or predetermined amount or by 1, and
in a case where the number of the objects is less than N, then set the counter to zero and repeat steps (c)-(g) with another frame or a subsequent frame of the plurality of frames; and
(h) trigger pullback in a case where the counter is X or greater, wherein X is a predetermined value, or, in a case where the counter has been increased by the one or more processors and the counter is less than X, repeat steps (c)-(g) with a next frame of the plurality of frames.

2. The device of claim 1, wherein the one or more processors further operate to one or more of the following:
  (i) prepare the plurality of A-lines, the image, or the images by deleting the imaging probe and extravascular noise from a current frame or image or otherwise perform frame or image processing or pre-processing, and set the counter to zero;
  (ii) perform frame or image processing or pre-processing on the A-lines, image, or images, by deleting one or more of: the imaging probe and/or extravascular noise from a current frame or image;
  (iii) segment the A-lines, a one frame or a current frame, the image, or the images using automatic thresholding, and separate the A-lines, the one frame or the current frame, the image or the images into four equal parts which correspond to four Cartesian quadrants while separating the A-lines, the image, or the images into three or more equal parts;
  (iv) delete any detected object of a predetermined size, and count how many objects are above or over a specific or predetermined distance from the imaging probe or count how many objects overlap with the BIA;
  (v) delete any detected object of a predetermined size, and count how many objects are above or over a specific or predetermined distance from the imaging probe or count how many objects overlap with the BIA and in a case where at least three (3) objects are detected above or over the imaging probe distance as the specific or the predetermined distance or are not overlapping with the BIA, then perform the counting step by increasing the counter to one or by one, or, in a case where at least three (3) objects are not detected above or over the imaging probe distance or are overlapping with the BIA, set the counter again to zero, and move to the next frame or image such that the one or more processors operate to repeat the steps (c)-(g); and/or
  (vi) in a case where the counter is not yet equal to or greater than the predetermined value X, then move to the next A-line frame or image and repeat the importing and the steps (c)-(g), or, in a case where the counter is equal to or greater than the predetermined value X, then trigger the automatic pullback of a catheter or probe of the imaging device via step (h) by ending a signal, by using a signal, or by generating or transmitting a signal.

3. The device of claim 2, wherein one or more of the following:
  (i) the object of the predetermined size is at least one of the following: a small object; and/or is an object corresponding to noise, residual blood, and/or other artifact(s);
  (ii) the one or more processors further operate to delete any detected object of a predetermined size, and count how many objects are above a specific or predetermined distance from the imaging probe or count how many objects overlap with the BIA, where the specific or predetermined distance from the imaging probe is defined as an imaging probe distance, and the one or more processors further operate to compare the objects to the imaging probe distance value to decide whether the objects belong to blood or not;
  (iii) the one or more processors further operate to delete any detected object of a predetermined size, and count how many objects are above a specific or predetermined distance from the imaging probe or count how many objects overlap with the BIA, and/or to define an imaging probe distance, the one or more processors further operate to measure an imaging depth at different blood state images or frames, and average the measurements; and/or
  (iv) the specific or predetermined distance is defined by using images with blood presence.

4. The device of claim 1, wherein one or more of the following:
  (i) the one or more processors further operate to calculate a relative position of object(s) from the imaging probe;
  (ii) the one or more processors further operate to calculate a relative position of object(s) from the imaging probe, and/or the one or more processors further operate to omit the calculation of the relative position of object(s) from the imaging probe;
  (iii) in a case where the one or more processors use the BIA, the BIA is denoted as an area above a specific distance from a tip of the imaging probe or a circular area above the imaging probe tip is denoted as the BIA;
  (iv) the BIA is defined or predefined using images with the blood being present; and/or
  (v) a number of pixels that are above a specific height from the imaging probe tip are denoted.

5. The device of claim 1, wherein one or more of the following:
  (i) the plurality of A-lines, the image, or the images are imported in a scan mode where the imaging probe is a full speed spinning imaging probe;
  (ii) the predetermined value X for the counter is at least one of the following: 1, 2, 3, 4, 5, 6, or more than 6, and/or is a number determined by a clinician based on how much time the pullback needs for a procedure or for imaging and on how long a clearance state lasts;
  (iii) the one or more processors further operate to detect how many objects are moved over blood imaging for Optical Coherence Tomography (OCT);
  (iv) the one or more processors further operate to decide or evaluate a clearing condition of the processed frame, A-lines, or image(s);
  (v) the plurality of A-lines, the image, or the images are imported in a scan mode where the imaging probe is a full speed spinning imaging probe and in a case where a number of objects over a specific or predetermined distance from the imaging probe are equal to or greater than a predetermined threshold, the one or more processors determine that a vessel wall or target in the image or frame is visible in the current image or frame; and/or
  (vi) the plurality of A-lines, the image, or the images are imported in a scan mode where the imaging probe is a full speed spinning imaging probe and in a case where a number of objects over a specific or predetermined distance from the imaging probe are equal to or greater than a predetermined threshold, the one or more processors determine that a vessel wall or target in the image or frame is visible in the current image or frame, and the predetermined threshold is one or more of the following: 2 or more, 3 or more, 4 or more, 5 or more, and/or a predetermined number or more where the predetermined number is set by a user of the device or automatically set by the device.

6. The device of claim 1, wherein one or more of the following:
  (i) the one or more processors further operate to control the device to flush the imaging probe to remove blood presence;

(ii) the one or more processors further operate to control the device to flush the imaging probe to remove blood presence, and the one or more processors further operate to ensure that the flushing and the automatic pullback are synchronized;

(iii) the one or more processors further operate to reduce, merge, and/or minimize one or more tasks of a user of the device during catheterization or imaging probe procedure(s) such that an effort of the user is also reduced, minimized, and/or made more efficient;

(iv) the one or more processors further operate to reduce, merge, and/or minimize one or more tasks of a user of the device during catheterization or imaging probe procedure(s) such that an effort of the user is also reduced, minimized, and/or made more efficient, and the tasks of the user involve one or more of the following: controlling live mode speed, pressing a button to control the live mode speed, controlling scan mode speed, pressing a button to control the scan mode speed, causing the flushing to occur, pushing a button to cause the flushing to occur, causing the pullback to occur, and/or pushing a button to cause the pullback to occur; and/or (v) the one or more processors further operate to trigger the automatic pullback of a catheter or probe of the imaging device without any user interaction.

7. The device of claim 1, wherein one or more of the following:

(i) the A-line(s), frame(s), or image(s) is/are defined by a block or set of A-lines and forms/form a two-dimensional (2D) Optical Coherence Tomography (OCT) image(s) or frame(s) when translated to Cartesian coordinates;

(ii) during image or frame processing or pre-processing, pixels which correspond to the imaging probe, an artifact, and/or extravascular tissue areas are set to zero by the one or more processors, and the one or more processors apply filtering;

(iii) during image or frame processing or pre-processing, pixels which correspond to the imaging probe, an artifact, and/or extravascular tissue areas are set to zero by the one or more processors, and the one or more processors apply filtering, and the filtering is a mean filtering, a spatial filter, and/or a sliding window or kernel spatial filter, which replaces a central value of the window with a mean intensity value of the pixels that belong to the window, and, for an image I and a window having size N×N, the value of the window's central pixel (i,j) is replaced by the $$M_N : \frac{1}{N \times N} \Sigma_{m,n \in N \times N} I(m, n),$$

where m, n are the pixels belonging to the window N×N; and/or (iv) during image or frame processing or pre-processing, pixels which correspond to the imaging probe, an artifact, and/or extravascular tissue areas are set to zero by the one or more processors, and the one or more processors apply filtering, and the filtering is Gaussian filtering or bilateral filtering, and/or the one or more processors further operate to use convolutions to replace an intensity of a central pixel of a mask with a weighted average of intensities of the neighborhood pixels.

8. The device of claim 1, wherein one or more of the following:

(i) the one or more processors further operate to apply image or frame segmentation by (a) applying automatic thresholding to the A-line(s), image, images, or frame(s), (b) smoothing the segmented A-line(s), image, images, or frame(s) by deleting the objects of a predetermined or set size that correspond to image or frame artifacts, and (c) separating the A-line(s), image, images, or frame(s) into the three or more equal parts;

(ii) the one or more processors further operate to apply image or frame segmentation by (a) applying automatic thresholding to the A-line(s), image, images, or frame(s), (b) smoothing the segmented A-line(s), image, images, or frame(s) by deleting the objects of a predetermined or set size that correspond to image or frame artifacts, and (c) separating the A-line(s), image, images, or frame(s) into the three or more equal parts, and the automatic thresholding is Otsu's thresholding;

(iii) the one or more processors further operate to apply image or frame seqmentatiuon by (a) applying automatic thresholding to the A-line(s), image, images, or frame(s), (b) smoothing the segmented A-line(s), image, images, or frame(s) by deleting the objects of a predetermined or set size that correspond to image or frame artifacts, and (c) separating the A-line(s), image, images, or frame(s) into the three or more equal parts, the automatic thresholding is Otsu's thresholding, a threshold $Thr_{otsu}$ for an image I is calculated using the Otsu's method, and the pixels of the image I that are smaller than $Thr_{otsu}$ are set to zero value such that a binary image is generated having arterial wall and blood represented by non-zero objects; where the image I corresponds to the A-line(s), the image, the images, or the frame(s);

(iv) to determine whether non-zero objects corresponding to image or frame artifacts exist and to remove the non-zero objects corresponding to image or frame artifacts from a set of non-zero objects to be used for detecting a border, the one or more processors further operate to detect objects that are smaller than a predetermined area to ensure that only objects remaining in the set correspond to a wall area and are to be used or are used to detect the border;

(v) to determine whether non-zero objects corresponding to image or frame artifacts exist and to remove the non-zero objects corresponding to image or frame artifacts from a set of non-zero ojbects to be used for detecting a border, the one or more processors further operate to detect objects that are smaller than a predetermined area to ensure that only objects remaining in the set correspond to a wall area and are to be used or are used to detect the border, and the predetermined area is a whole catheter area or a probe area or is 3% of the whole image or frame; and/or (vi) the one or more processors further operate to detect a larger object and delete the objects which are smaller than the larger object by a predetermined percentage, where the predetermined percentage is one or more of the following: 24%, 20%, 25%, 30%, any value in the range of about 10% to about 50%, any value in the range of 10% to 50%, any value in the range of about 20% to about 30%, and/or any value in the range of 20% to 30%.

9. The device of claim 1, wherein one or more of the following:
   (i) the one or more processors further operate to, for a predetermined number of frames or images in a row, determine whether a target or an arterial wall is visible;
   (ii) the one or more processors further operate to, for a predetermined number of frames or images in a row, determine whether a target or an arterial wall is visible, and the predetermined number of frames or images in a row is one or more of the following: three, four, five, and/or six;
   (iii) the one or more processors further operate to, for a predetermined number of frames or images in a row, determine whether a target or an arterial wall is visible, and in a case where the target or the arterial wall is visible, the one or more processors trigger the automatic pullback;
   (iv) the counter operates to ensure that blood is cleared enough so the automatic pullback is synchronized with an improved or optimal clearing state;
   (v) the counter is increased each time a clearance state is detected; and/or
   (vi) the one or more processors further operate to, for a predetermined number of frames or images in a row, determine whether a target or an arterial wall is visible, and the one or more processors further operate to detect whether a number of non-overlapping to BIA objects is greater than a predetermined threshold such that it is determined that the target or arterial wall is revealed or visible and such that the blood is flushed to indicate a clearance state, wherein the predetermined threshold is three or more or greater than three.

10. A method for triggering an automatic pullback in an imaging device having an imaging probe, the method comprising:
   (a) importing a plurality of A-lines, an image, or images;
   (b) initializing a counter;
   (c) segmenting the A-lines, the image, or the images;
   (d) separating the segmented A-lines, image, or images into three or more equal parts;
   (e) defining a Blood Imaging Area (BIA), which is an area surrounding the imaging probe in a case where blood is present;
   (f) detecting a number of objects that are non-overlapping with the BIA, or that are above or over a specific or predetermined distance from the imaging probe, within one frame or a current frame of a plurality of frames of the segmented A-lines, image, or images;
   (g) performing a counting step:
      in a case where the number of the objects is greater than or equal to N, wherein N is a minimum acceptance number of objects that define a partial cleared or cleared state, then increasing the counter by a set or predetermined amount or by 1, and
      in a case where the number of the objects is less than N, then setting the counter to zero and repeating steps (c)-(g) with another frame or a subsequent frame of the plurality of frames; and
   (h) triggering pullback in a case where the counter is X or greater, wherein X is a predetermined value, or, in a case where the counter has been increased and the counter is less than X, repeating steps (c)-(g) with a next frame of the plurality of frames.

11. The method of claim 10, further comprising one or more of the following:
   (i) preparing the plurality of A-lines, the image, or the images by deleting the imaging probe and extravascular noise from a one frame or a current frame or image or otherwise perform frame or image processing or pre-processing, and setting the counter to zero;
   (ii) performing frame or image processing or pre-processing on the A-lines, image, or images, by deleting one or more of: the imaging probe and/or extravascular noise from a current frame or image;
   (iii) segmenting the A-lines, the one frame or the current frame, the image, or the images using automatic thresholding, and separating the A-lines, the one frame or the current frame, the image or the images into four equal parts which correspond to four Cartesian quadrants while separating the A-lines, the image, or the images into three or more equal parts;
   (iv) deleting any detected object of a predetermined size, and counting how many objects are above or over a specific or predetermined distance from the imaging probe or counting how many objects overlap with the BIA;
   (v) deleting any detected object of a predetermined size, counting how many objects are above or over a specific or predetermined distance from the imaging probe or counting how many objects overlap with the BIA, and in a case where at least three (3) objects are detected above or over an imaging probe distance as a specific or predetermined distance from the imaging probe or are not overlapping with the BIA, then performing the counting step by increasing the counter to one or by one, or, in a case where at least three (3) objects are not detected over the imaging probe distance or are overlapping with the BIA, setting the counter again to zero, and moving to the next frame or image such that the steps (c)-(g) are repeated; and/or
   (vi) in a case where the counter is not yet equal to or greater than the predetermined value X, then moving to the next A-line frame or image and repeating the importing and the steps (c)-(g), or, in a case where the counter is equal to or greater than the predetermined value X, then triggering the automatic pullback of a catheter or probe of the imaging device via step (h) by ending a signal, by using a signal, or by generating or transmitting a signal.

12. The method of claim 11, wherein one or more of the following:
   (i) the method further comprises deleting any detected object of a predetermined size, and counting how many objects are above or over a specific or predetermined distance from the imaging probe or counting how many objects overlap with the BIA, and the object of the predetermined size is at least one of the following: a small object; and/or is an object corresponding to noise, residual blood, and/or other artifact(s);
   (ii) the method further comprises deleting any detected object of a predetermined size, and counting how many objects are above or over a specific or predetermined distance from the imaging probe or counting how many objects overlap with the BIA, and the specific or predetermined distance from the imaging probe is defined as imaging probe distance, and the method further comprises comparing the objects to the imaging probe distance value to decide whether the objects belong to blood or not;
   (iii) the method further comprises deleting any detected object of a predetermined size, and counting how many objects are above or over a specific or predetermined distance from the imaging probe or counting how many objects overlap with the BIA, and/or to define an imaging probe distance as a specific or predetermined distance from the imaging probe, the method further comprises measuring an imaging depth at different blood state images or frames, and averaging measurements; and/or (iv) the method further comprises deleting any detected object of a predetermined size, and counting how many objects are above or over a specific or predetermined distance from the imaging probe or counting how many objects overlap with the BIA, and the specific or predetermined distance is defined by using images with blood presence.

13. The method of claim 10, wherein one or more of the following:

(i) the method further comprises calculating a relative position of object(s) from the imaging probe;

(ii) the method further comprises calculating a relative position of object(s) from the imaging probe, and/or the method further comprises omitting the calculation of the relative position of object(s) from the imaging probe;

(iii) in a case where the BIA is used, the BIA is denoted as an area above a specific distance from a tip of the imaging probe or a circular area above the imaging probe tip is denoted as the BIA;

(iv) the BIA is defined or predefined using images with the blood being present; and/or (v) a number of pixels that are above a specific height from the imaging probe tip are denoted.

14. The method of claim 10, wherein one or more of the following:

(i) the plurality of A-lines, the image, or the images are imported in a scan mode where the imaging probe is a full speed spinning imaging probe;

(ii) the predetermined value X for the counter is at least one of the following: 1, 2, 3, 4, 5, 6, or more than 6, and/or is a number determined by a clinician based on how much time the pullback needs for a procedure or for imaging and on how long a clearance state lasts;

(iii) the method further comprises detecting how many objects are moved over blood imaging for Optical Coherence Tomography (OCT);

(iv) the method further comprises deciding or evaluating a clearing condition or clearance condition of the processed frame, A-lines, or image(s);

(v) in a case where a number of objects over an imaging probe distance as a specific or predetermined distance from the imaging probe are equal to or greater than a predetermined threshold, the method further comprises determining that a vessel wall or target in the image or frame is visible in the current image or frame; and/or (vi) in a case where a number of objects over an imaging probe distance as a specific or predetermined distance from the imaging probe are equal to or greater than a predetermined threshold, the method further comprises determining that a vessel wall or target in the image or frame is visible in the current image or frame, and the predetermined threshold is one or more of the following: 2 or more, 3 or more, 4 or more, 5 or more, and/or a predetermined number or more where the predetermined number is set by a user of the imaging probe or is automatically set or loaded by the method.

15. The method of claim 10, wherein one or more of the following:

(i) the method further comprises flushing the imaging probe to remove blood presence;

(ii) the method further comprises flushing the imaging probe to remove blood presence, and the method further comprises ensuring that the flushing and the automatic pullback are synchronized or performs the flushing and the automatic pullback in synchronized fashion;

(iii) the method further comprises reducing, merging, and/or minimizing one or more tasks of a user of the imaging probe during a catheterization or imaging probe procedure(s) such that an effort of the user is also reduced, minimized, and/or made more efficient;

(iv) the method further comprises reducing, merging, and/or minimizing one or more tasks of a user of the imaging probe during a catheterization or imaging probe procedure(s) such that an effort of the user is also reduced, minimized, and/or made more efficient, and the tasks of the user involve one or more of the following: controlling live mode speed, pressing a button to control the live mode speed, controlling scan mode speed, pressing a button to control the scan mode speed, causing the flushing to occur, pushing a button to cause the flushing to occur, causing the pullback to occur, and/or pushing a button to cause the pullback to occur; and/or (v) the method further comprises triggering the automatic pullback of a catheter or probe of the imaging device without any user interaction.

16. The method of claim 10, wherein one or more of the following:

(i) the A-line(s), frame(s), or image(s) is/are defined by a block or set of A-lines and forms/form a two-dimensional (2D) Optical Coherence Tomography (OCT) image(s) or frame(s) when translated to Cartesian coordinates;

(ii) the method further comprises, during image or frame processing or pre-processing, setting pixels which correspond to the imaging probe, an artifact, and/or extravascular tissue areas to zero, and applying filtering;

(iii) the method further comprises, during image or frame processing or pre-processing, setting pixels which correspond to the imaging probe, an artifact, and/or extravascular tissue areas to zero, and applying filtering, and the filtering is a mean filtering, a spatial filter, and/or a sliding window or kernel spatial filter, which replaces a central value of the window with a mean intensity value of the pixels that belong to the window, and, for an image I and a window having size N×N, the value of the window's central pixel (i,j) is replaced by the $$M_N : \frac{1}{N \times N} \Sigma_{m,n \in N \times N} I(m, n),$$

where m, n are the pixels belonging to the window N×N; and/or (iv) the method further comprises, during image or frame processing or pre-processing, setting pixels which correspond to the imaging probe, an artifact, and/or extravascular tissue areas to zero, and applying filtering, and the filtering is Gaussian filtering or bilateral filtering, and/or the method further comprises using convolutions to replace an intensity of a central pixel of a mask with a weighted average of intensities of neighborhood pixels.

17. The method of claim 10, wherein one or more of the following:
  (i) the method further comprises applying image or frame segmentation by (a) applying automatic thresholding to the A-line(s), image, images, or frame(s), (b) smoothing the segmented A-line(s), image, images, or frame(s) by deleting the objects of a predetermined or set size that correspond to image or frame artifacts, and (c) separating the A-line(s), image, images, or frame(s) into the three or more equal parts;
  (ii) the method further comprises applying image or frame segmentations by (a) applying automatic thresholding to the A-line(s), image, images, or frame(s), (b) smoothing the segmented A-line(s), image, images, or frame(s) by deleting the objects of a predetermined or set size that correspond to image or frame artifacts, and (c) separating the A-line(s), image, images, or frame(s) into the three or more equal parts, and the automatic thresholding is Otsu's thresholding;
  (iii) the method further comprises applying image or frame seqmentation by (a) applying automatic thresholding to the A-line(s), image, images, or frame(s), (b) smoothing the seqmented A-line(s), image, images, or frame(s) by deleting the objects of a predetermined or set size that correspond to image or frame artifacts, and (c) separating the A-line(s), image, images, or frame(s) into the three or more equal parts, the automatic thresholding is Otsu's thresholding, threshold $Thr_{otsu}$ for an image I is calculated using the Otsu's method, and the pixels of the image I that are smaller than $Thr_{otsu}$ are set to zero value such that a binary image is generated having arterial wall and blood represented by non-zero objects, where the image I corresponds to the A-line(s), image, images, or frame(s);
  (iv) to determine whether non-zero objects corresponding to image or frame artifacts exist and to remove the non-zero objects corresponding to image or frame artifacts from a set of non-zero objects to be used for detecting a border, the method further comprises detecting objects that are smaller than a predetermined area to ensure that only objects remaining in the set correspond to a wall area and are to be used or are used to detect the border;
  (v) to determine whether non-zero objects corresponding to image or frame artifacts exist and to remove the non-zero objects corresponding to image or frame artifacts from a set of non-zero objects to be used for detecting a border, the method further comprises detecting objects taht are smaller than a predetermined area to ensure that only objects remaining in the set correspond to a wall area and are to be used or are used to detect the bored, and the predetermined area is a whole catheter area or an imaging probe area or is 3% of the whole image or frame; and/or
  (vi) the method further comprises detecting a larger object and deleting the objects which are smaller than the larger object by a predetermined percentage, where the predetermined percentage is one or more of the following: 24%, 20%, 25%, 30%, any value in the range of about 10% to about 50%, any value in the range of 10% to 50%, any value in the range of about 20% to about 30%, and/or any value in the range of 20% to 30%.

18. The method of claim 10, wherein one or more of the following:
  (i) the method further comprises, for a predetermined number of frames or images in a row, determining whether a target or an arterial wall is visible;
  (ii) the method further comprises, for a predetermined number of frames or images in a row, determining whether a target or an arterial wall is visible, and the predetermined number of frames or images in a row is one or more of the following: three, four, five, and/or six;
  (iii) the method further comprises, for a predetermined number of frames or images in a row, determining whether a target or an arterial wall is visible, and in a case where the target or the arterial wall is visible, the method triggers the automatic pullback;
  (iv) the counter operates to ensure that blood is cleared enough so the automatic pullback is synchronized with an improved or optimal clearing state;
  (v) the counter is increased each time a clearance state is detected; and/or
  (vi) the method further comprises, for a predetermined number of frames or images in a row, determining whether a target or an arterial wall is visible, and the method further comprises detecting whether a number of non-overlapping to BIA objects is greater than a predetermined threshold such that it is determined that the target or arterial wall is revealed or visible and such that the blood is flushed to indicate a clearance state, wherein the predetermined threshold is three or more or greater than three.

19. A non-transitory computer-readable storage medium storing at least one program for causing a computer to execute a method for triggering an automatic pullback, the method comprising:
  (a) importing a plurality of A-lines, an image, or images;
  (b) initializing a counter;
  (c) segmenting the A-lines, the image, or the images;
  (d) separating the segmented A-lines, image, or images into three or more equal parts;
  (e) defining a Blood Imaging Area (BIA), which is an area surrounding the imaging probe in a case where blood is present;
  (f) detecting a number of objects that are non-overlapping with the BIA, or that are above or over a specific or predetermined distance from the imaging probe, within one frame or a current frame of a plurality of frames of the segmented A-lines, image, or images;
  (g) performing a counting step:
    in a case where the number of the objects is greater than or equal to N, wherein N is a minimum acceptance number of objects that define a partial cleared or cleared state, then increasing the counter by a set or predetermined amount or by 1, and
    in a case where the number of the objects is less than N, then setting the counter to zero and repeating steps (c)-(g) with another frame or a subsequent frame of the plurality of frames; and
  (h) triggering pullback in a case where the counter is X or greater, wherein X is a predetermined value, or, in a case where the counter has been increased and the counter is less than X, repeating steps (c)-(g) with a next frame of the plurality of frames.

* * * * *